(12) United States Patent
Brandt et al.

(10) Patent No.: US 6,228,873 B1
(45) Date of Patent: *May 8, 2001

(54) METHOD FOR ENHANCING OUTFLOW OF AQUEOUS HUMOR IN TREATMENT OF GLAUCOMA

(75) Inventors: James D. Brandt, Folsom; Martha E. O'Donnell; Fitz-Roy E. Curry, both of Davis, all of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/093,961

(22) Filed: Jun. 8, 1998

Related U.S. Application Data

(63) Continuation-in-part of application No. 08/353,442, filed on Dec. 9, 1994, now Pat. No. 5,585,401.
(51) Int. Cl.$^7$ .................................................. A01N 43/40
(52) U.S. Cl. .......................... 514/347; 514/471; 514/428
(58) Field of Search .................................. 514/347, 428, 514/471, 562

(56) References Cited

U.S. PATENT DOCUMENTS

| | | | |
|---|---|---|---|
| 4,757,089 | 7/1988 | Epstein | 514/571 |
| 4,861,786 | 8/1989 | Demmer et al. | 514/347 |
| 4,895,807 | 1/1990 | Cherksey | 436/63 |

FOREIGN PATENT DOCUMENTS

| | | |
|---|---|---|
| 0 628 313 | 12/1994 | (EP) . |
| WO 95/20568 | 8/1995 | (WO) . |
| WO 96/16647 | 6/1996 | (WO) . |

OTHER PUBLICATIONS

Leung, et al., J. Biol. Chem. 269(14), pp. 10581–10589 (Apr. 8, 1994).

Masereel, et al., "Design, Synthesis and Biological Activity of a Series of Torasemide Derivatives, Potent Blockers of the NA+2Cl–K+ Co–transporter: In–vitro Study," J. Pharm. Pharmacol., 44:589–593, 1992.

R. Greger, P. Wangermann, "Loop Diuretics," Renal Physiol., Basel 10:174–183, 1987.

Brandt, et al., "The Capillary Endothelium as an Experiment Model of the Outflow Pathways of the Eye," Invest. Ophthalmol. Vis. Sci., 35(4[Suppl]):1848, 1994.

Palfrey, et al., "Inhibition of Na–K–2Cl cotransport and bumetanide binding by ethacrynic acid, its analogues, and adducts," Am. J. Physiol., 264:C1270–C1277, 1993.

Edelman et al., "Ion Transport Asymmetry and Functional Coupling in Bovine Pigmented and Nonpigmented Ciliary Epithelial Cells", Am. J. Physiol., vol. 266, pp. C1210–C1221 (1994).

Peczon et al., "Diuretic Drugs in Glaucoma", Am. J. Ophth., vol. 66, No. 4, pp. 681–683 (1968).

D'Onofrio et al., "Associative Treatment of Intraocular Pressure via Neuroleptanalgesia in Open–Bulb Surgery", Acta Anaesth. Ital., vol. 32, No. 1, pp. 147–156 (1981) English Translation Provided.

Da Ros et al., "Use of Furosemide in the Treatment of Acute Glaucoma Attacks", Boll. Ocul., vol. 58, No. 5–6, pp. 335–348 (1979) English Translation Provided.

*Primary Examiner*—Phyllis G. Spivack
(74) *Attorney, Agent, or Firm*—Fish & Richardson P.C.

(57) ABSTRACT

Elevated intra-ocular pressure is reduced by administration directly to the eye of compounds that inhibit function of a $Na^+$—$K^+$—$2Cl^{-2}$ cotransporter mechanism discovered in trabecular meshwork cells of mammalian eyes. These compounds are useful in treatment of diseases of the eye associated with elevated intra-ocular pressure, such as ocular hypertension and glaucoma. A screening method is provided to discover additional compounds with utility for lowering intra-ocular pressure by substantially inhibiting the $Na^+$—$K^+$—$Cl^{-2}$ cotransporter mechanism in trabecular meshwork cells.

22 Claims, 8 Drawing Sheets

METHOD FOR ENHANCING OUTFLOW OF AQUEOUS HUMOR IN TREATMENT OF GLAUCOMA

This application is a continuation-in-part of U.S. patent application Ser. No. 08/353,442, filed on Dec. 9, 1994, now U.S. Pat. No. 5,585,401.

BACKGROUND OF THE INVENTION

1. Field of the Invention

This invention relates to methods for reducing the intra-ocular pressure of the eye by enhancing aqueous humor outflow, and to a method for screening compounds that reduce intra-ocular pressure.

2. Description of Related Art

In glaucoma, a leading cause of blindness, the optic nerve is damaged through a poorly-understood interaction of elevated intra-ocular pressure (IOP) and patient predisposition to the disease. In the most common form of glaucoma the trabecular meshwork (TM), which plays a critical role in regulation of aqueous humor outflow and intra-ocular pressure in both health and disease, is thought to be defective in such a manner that resistance to outflow and IOP both rise.

The anterior chamber of the eye is bathed with aqueous humor, formed continuously by the ciliary body. Aqueous humor moves by bulk flow from its site of production in the posterior chamber through the pupillary aperture and into the anterior chamber. It subsequently exits the anterior chamber via one of two routes.

The majority of outflow in the healthy human eye occurs at the anterior chamber angle. where aqueous humor passes through the trabecular meshwork and into the Canal of Schlemrnm, from where it joins the general venous drainage of the eye. A second outflow pathway is via the uveoscleral route, although this appears to be a minor ($\approx$20%) pathway in the normal human eye. A homeostatic balance of aqueous humor production and drainage allows intra-ocular pressure to be maintained within narrow limits in the normal eye (Caprioli, J., *Adler's Physiology of the Eye: Clinical Application*, W. M. Hart, ed. 9th Ed., 7:228–247, 1992; Hart, W. M., *Adler's Physiology of the Eye: Clinical Application*, W. M. Hart, ed. 9th Ed., 8:248–267, 1992).

Production of aqueous humor occurs along the surface of the ciliary processes (par splicata), which is covered by a double layer of epithelial cells consisting of a pigmented and non-pigmented layer situated with their apical surfaces juxtaposed. These function in tandem to produce transepithelial secretion of NaCl and water in movement from the blood to the aqueous humor. Evidence has been provided that Na—K—Cl cotransport and the Na/K pump act in concert to bring about the vectorial transport (Dong, et al., *Invest. Ophthalmol. Vis. Sci.*, 35:1660, 1994). The rate of aqueous humor production is quite high relative to other types of epithelia that function in vectorial transport of water and electrolytes. Thus, a drainage pathway that can accommodate this rate of fluid production is essential for maintenance of normal intra-ocular pressure. The aqueous humor production and drainage mechanisms work to replace the entire volume of aqueous every 100 minutes (Caprioli, J., supra).

It is well recognized that regulation of aqueous humor outflow through the trabecular meshwork is critically important for maintenance of an appropriate intra-ocular pressure, and that in disease states such as ocular hypertension and glaucoma, this regulation appears to be defective. For instance, U.S. Pat. No. 4,757,089 teaches a method for increasing aqueous humor outflow by topical or intracameral administration of ethacrynic acid, or an analog, to treat glaucoma. It is also known that ethacrynic acid increases water flux across the walls of perfused microvessels (Brandt, et al., *Invest. Ophthalmol. Vis. Sci.*, 35(4[Suppl]):1848, 1994) and inhibits $Na^+$—$K^+$— $2Cl^-$ cotransport activity of avian erythrocytes (Palfrey, et al., *Am. J Physiol.*, 264:C1270–1277, 1993), although the mechanisms by which these phenomena occur have not been elucidated. For instance, phenoxyacetic acids inhibit NaCl reabsorption in the thick ascending limb of the loop of Henle screening test, but its effect was exerted from both epithelial sides, rather than from the luminal side as with the class of loop diuretics, and it led to a depolarization of the membrane voltage. This effect is compatible with an inhibitory action at the level of mitochondrial ATP production rather than an inhibition of the $Na^+$—$K^+$—$2Cl^-$ cotransporter.

In contrast to the current level of knowledge regarding cellular processes responsible for aqueous humor production by the ciliary body, relatively little is known about the cellular mechanisms in the trabecular meshwork that determine the rate of aqueous outflow. Pinocytotic vesicles are observed in the juxtacanalicular meshwork and the inner wall of Schlemm's Canal. The function of these vesicles remains unknown, but some investigators have suggested that the bulk flow of aqueous humor through the meshwork cannot be accounted for by flow through the intercellular spaces and that these vesicles play a central role in outflow regulation. Evidence has been provided that cytoskeleton-mediated changes in trabecular meshwork cell shape modulate aqueous outflow (Erickson-Lamy and Nathanson, *Invest. Ophihalmol. Vis. Sci.*, 33:2672–2678, 1992; Enckson-Lamy, Schroder, and Epstein, *Invest. Opthalmol. Vis. Sci.*, 33:2631–2640, 1992). The extracellular matrix surrounding the trabeculae is thought to contribute to outflow resistance, perhaps by interactions with proteins contained in the aqueous humor (Freddo, T. F., *Optometry Vis. Sci.*, 70:263–270, 1993). Indeed, abnoniailities in this extra-cellular matrix may contribute to the increased outflow resistance seen in corticosteroid-induced glaucoma (Partridge, et al., Invest. *Ophithalmol. Vis. Sci.*, 30:1843–1847, 1989; Polansky, et aL, *The Ocular Effects of Prostaglandins and Other Eicosanoids*, Alan R. Liss, Inc., pp. 113–138, 1989). Investigators evaluating both normal physiology and drug effects have provided evidence that changes in cell shape (as distinct from cell volume) may be involved in outflow regulation (Erickson-Lamy and Nathanson, supra; Erickson-Lamy, Schroder, and Epstein, supra). Trabecular meshwork cells have been shown to possess actin and myosin filaments (Clark, et al., *Invest. Ophthalmol. Vis. Sci.*, 35:281–294, 1994) and to contract in response to some agents (Coroneo, et al., *Exp. Eye Res.*, 52:375–388, 1990; Lepple-Wienhues, et al., *Exp. Eye Res.*, 53:33–38, 1991; Wiederholt, et al., *Invest. Ophthalmol. Vis. Sci.*, 35:2515–2520, 1994). In a review of the existing literature at the time, Davson speculated that changes in trabecular meshwork cell volume (as distinct from cell shape) may participate in the regulation of aqueous outflow facility (Davson, H., *Physiology of the Eye*, H. Davson, ed., 5th Ed., Macmillan Press, London, Chapter 1, pp. 9–81, 1990), but to date this hypothesis has not been specifically addressed by other investigators. An excellent review of trabecular meshwork physiology and morphology is found in P. L. Kaufinan, "Pressure-dependent Outflow" in R. Ritch et al., ed. *The Glaucomas*. St. Louis, Mo.; C.V. Mosby Co., 1989, 219–240, Vol. 1.

In addition to regulation of aqueous outflow, trabecular meshwork cells are thought to serve an immunologic function as they phagocytize antigens in the anterior chamber of the eye as they pass through the trabecular meshwork (Epstein, et al., *Ivest. Opthalmol. Vis. Sci.*, 27:387–395, 1986). It has been hypothesized that the cells then migrate out of the meshwork into the Canal of Schlemm to enter the systermic circulation and act as antigen presenting cells to trigger the production of antibodies to the phagocytized antigen. In at least one form of glaucoma (pigmentary), this phagocytotic function is thought to be overwhelmed, resulting in increased resistance to aqueous outflow (Epstein, et al., supra). The endothelial cells lining the Canal of Schlemm also appear to contribute to the resistance to outflow in the normal eye (Davson, H., supra; Hart, W. M., supra).

A number of hormones and neurotransmitters have been documented to decrease intra-ocular pressure by modulating aqueous production or outflow. Studies employing a human eye perfusion model have shown that epinephrine, via an apparent β-adrenergic effect upon the uveo-scleral pathway, increases the facility of outflow (Erickson-Lamy and Nathanson, supra). Nitrovasodilators have been found to increase outflow facility and decrease intra-ocular pressure in monkey eye (Schuman, et al., *Exp. Eye Res.*, 58:99–105, 1994). Similarly, atrial natriuretic peptide decreases intra-ocular pressure in monkey eyes and increases aqueous humor production (Samuelsson-Almen, et al., *Exp. Eye Res.*, 53:253–260, 1991). In addition to these hormones and neurotransmitters, ethacrynic acid has been shown to increase aqueous outflow and decrease intra-ocular pressure by modulating aqueous inflow and outflow. Elevations of norepinephrine concentration in the aqueous humor resulting from cervical sympathetic nerve stimulation cause an increase in intra-ocular pressure of rabbit eye in situ by a mechanism that appears to involve an α-adrenergic effect (Gallar, et al., *Invest. Ophthalmol. Vis. Sci.*, 34:596–605, 1993). Similarly, topical administration of vasopressin to the eye has been shown to increase intra-ocular pressure and decrease facility of outflow in both normal and glaucomatous human eyes (Becker, et al., *Arch. Ophthalmol.*, 56:1, 1956; Viggiano, et al., *Am. J. Ophthalmol.*, 115:511–516, 1993). A local renin-angiotensin system resides in the eye, and inhibition of angiotensin converting enzyme causes a decrease of intra-ocular pressure (Abrahms, et al., *J. Ocular Pharmacol.*, 7:41–51, 1991; Deinum, et al., *Endocrinol.*, 126:1673–1682, 1990). In contrast to these rapidly-acting agents, administration of the glucocorticoid dexamethasone increases resistance to outflow over a slower time course of hours and days, an effect that has been postulated to occur in the expression of extracellular matrix (Becker, et al, *Arch. Ophthalmol.*, 70:500–507, 1963; Clark, et al., supra; Partridge, et al., supra; Polansky, et al., supra).

Relatively little is known about the signal transduction and ion transport properties of TM cells. Cultured bovine trabecular meshwork cells have been examined for their ability to regulate intracellular pH (Chu, et al, *Acta Ophthalmol.*, 70:772–779, 1992). These studies demonstrated that the cells possess a Na/H exchanger that is activated by intracellular acidification and inhibited by amiloride, as is Na/H exchange of other cell types. In other studies of cultured bovine TM cells, Coroneo, et al,supra, have provided electrophysiological evidence that these cells also possess Na/K ATPase and K channels. The presence of Ca channels in these TM cells has been indicated by the observation that the Ca channel blocker nifedipine prevents endothelin-evoked depolarization of the cells (Lepple-Wienhues, et al, *German J. Ophthalmol.*, 1:159–163, 1992). In addition, both plasma membrane and sarcolemmal Ca ATPases have been identified in rabbit TM cells by cytochernical methods (Kobayashi, et al, *Acta Soc. Ophthalmol Jap.*, 93:396–403, 1989).

Na—K—Cl cotransport is a plasma membrane ion transport system found in a wide variety of cell types, both epithelial and non-epithelial (Chipperfield, A., *Clin. Sci.*, 71:465–476, 1986; Haas, M., *Ann. Rev. Physiol.*, 51:443–457, 1989; Pewitt, et al., *J. Biol. Chem.*, 265(34): 20747–20756, 1990). It is a bidirectional symport mechanism, indicating that each transport molecule binds to the three transported ion species (Na, K and Cl), and moves them together across the plasma membrane in the same direction. The transporter is bidirectional such that it can operate to move the ions into or out of the cell with the net direction of flux determined by the electrochemical gradients of Na, K and Cl. In many cells, the inwardly directed Na gradient is the most prominent, and net movement of these ions is directed into the cell (Chipperfield, A., supra; Haas, M., supra; O'Grady, et al., *Am. J. Physiol.*, 253:C177–C192, 1987). Other characteristic features of Na—K—Cl cotransport include: 1) a high ion selectivity for Na, K and Cl; 2) an absolute requirement for the presence of all three ion species to operate; and 3) specific inhibition by "loop" diuretics (Palfrey, et al., supra).

There are two types of Na—K—Cl cotransporters with different electroneutral stoichiometries. For most cells in which it has been studied (Ehrlich ascites tumor cells, rabbit kidney cells and duck red blood cells), the stoichiometry of cotransport is 1 $Na^+$:1 $K^+$:2 $Cl^-$, but in Squid axon the stoichiometry is different, 2 $Na^+$:1 $K^+$:3 $Cl^-$. Whereas the kinetic and pharmacological features of Na—K—Cl cotransport are quite constant among different cell types, the regulation of cotransport is heterogeneous. Elevation of intracellular cyclic AMP stimulates cotransport in some cells, while it inhibits cotransport in other cells. Similarly, elevation of cyclic GMP can have either stimulatory or inhibitory effects, and cotransport can be regulated by Ca and by phorbol esters, activators of protein kinase C (Chipperfield, A., supra; O'Donnell, et al., *Proc. Natl. Acad. Sci., USA*, 83:6132–6136, 1986, O'Donnell, etal., *Am. J. Physiol.*, 255:C169–C180, 1988; Grady, et al., supra). For instance, in cultured vascular endothelial cells, $Na^+$—$K^+$—$2Cl^-$ cotransport is inhibited by elevations of intracellular cyclic AMP and cyclic GMP, and by activation of protein kinase C . In contrast, elevation of intracellular Ca stimulates endothelial cell $Na^+$—$K^+$—$2Cl^-$ cotransport (O'Donnell, M. E., *Am. J. Physiol.*, 257:C36–C-44, 1989; O'Donnell, M. E., *J. Biol. Chem.*, 266:11559–11566, 1991). The reports of several studies have suggested that regulation of cotransport activity by vasoactive agonists and by extracellular tonicity involve a direct phosphorylation of the cotransporter (Lyle, et al., *J. Biol. Chem.*, 267:25428–25437, 1992; Pewitt, et al., supra; Torchia, et al., *J BioL Chem.*, 267:25444–25450, 1992).

Two primary physiological functions have been demonstrated for Na—K—Cl cotransport. The cotransporter participates in vectorial transport of ions across some epithelia, working in conjunction with the Na/K pump and other transport systems for Na, K and Cl (O'Grady, et al., supra). This function has been reported to occur in ciliary epithelial cells in the eye (Dong, et al, supra). The cotransporter also finctions to regulate cell volume in a number of cell types, both epithelial and non-epithelial, in response to varying extracellular osmolarity (Eveloff, et al., *Am. J. Physiol*, 252:F1–F10, 1987; Kobayashi, et al., supra, MacKnight, A.

D. C., *Renal Physiol. Biochem.*, 3–5:114–141, 1988; O'Donnell, M. E., *Am. J. Physiol.*, 264:1316–1326, 1993; O'Grady, et al., supra). When cells are exposed to hypertonic media, they shrink rapidly as water exits the cell down its concentration gradient. In cells that utilize Na—K—Cl cotransport to regulate volume, the shrinkage of cells activates the cotransporter, which in turn mediates a net uptake of Na, K and Cl into the cell. As water re-enters the cell with the transported ions, the cell swells again. The Na—K—Cl cotransport system performs this function in a number of cell types, including vascular endothelial cells, avian ernthrocytes, Ehrlich ascites tumor cells, human fibroblasts, chick cardiac cells, and cells of rabbit renal thick ascending limb (Kregenow, F. M., *Ann. Rev. Physiol.*, 43:493–505, 1981; MacKnight, A. D. C., supra; O'Donnell, M. E., supra, 1993). Trabecular meshwork and vascular endothelium both present highly regulated barriers to solute and water flux.

A regulatory volume increase can also be mediated in some cell types by combined actions of the Na/H exchange Cl/$HCO_3$ exchange systems (Kregenow, F. M., supra; MacKnight, A. D. C., supra). Exposure of cells to hypotonic media causes cells to swell rapidly as water enters the intracellular space, followed by a compensatory decrease in cell volume. The regulatory volume decrease appears to be mediated by a net efflux of ions through transporters separate from the Na—K—Cl cotransporter, for example the K and Cl conductive pathways (Eveloff, et al., supra; Kregenow, F. M., supra; MacKnight, A. D. C., supra). In addition, vasoactive agents have been shown to modulate the cell volume regulating system of avian erythrocytes. In these cells, the volume set point appears to be increased by catecholamines, such that the response of the Na—K—Cl cotransporter to extracellular tonicity is altered (Geck, et al., *J. Memb. Biol.*, 91:97–105, 1986).

The glaucomas comprise a heterogeneous group of eye diseases in which elevated IOP causes damage and atrophy of the optic nerve, resulting in vision loss. The underlying cause of the elevated IOP can be grossly divided into two pathophysiologic scenarios in which the drainage pathways are either physically closed off (as in the various forms of angle-closure glaucoma) or in which the drainage pathways appear anatomically normal but are physiologically dysfunctional (as in the various forms of open-angle glaucoma). Angle-closure glaucoma is nearly always a medical and/or surgical emergency, in which pharmacologic intervention is essential in controlling an acute attack. but in which the long-range management is usually surgical Primary Open Angle Glaucoma (POAG), on the other hand, has a gradual, symptomless onset and is usually treated with chronic drug therapy. POAG is the most common form of glaucoma, comprising ≈80% of newly-diagnosed cases in the USA, and is the leading cause of blindness among African Americans.

Drugs currently used to treat glaucoma can be divided into those that reduce aqueous humor inflow and those that enhance aqueous humor outflow. The most commonly-prescribed drugs at present are the β-adrenergic antagonists, which reduce aqueous humor inflow through an unknown effect on the ciliary body. Other drugs that reduce aqueous inflow include inhibitors of carbonic anhydrase (e.g., acetazolamide and methazolamide) and the alpha-adrenergic agonist apraclonidine; both of these drug classes exert their clinical effects through a poorly-understood action on the ciliary body. Each of these drugs, although effective in many patients, is poorly tolerated in some because of profound and occasionally life-threatening systemic adverse effects.

Drugs that enhance aqueous humor outflow from the eye include miotics and the adrenergic agonists. The miotics exert a mechanical effect on the longitudinal muscle of the ciliary body and thus pull open the trabecular meshwork; they comprise both direct-acting parasympathomimetic agents (e.g., pilocarpine and carbachol) and indirect-acting parasympathornimetic agents (e.g., echothiopate). Miotic agents are highly effective in lowering IOP but have significant adverse effects, including chronic miosis, decreased visual acuity, painful accomodative spasm and risk of retinal detachment. Adrenergic agonists (e.g., epinephrine and dipivefrin) act on the uveoscleral outflow tract to enhance outflow through a mechanism that remains poorly understood. These drugs have perhaps the best safety profile of the compounds presently used to treat glaucoma but are among the least effective in their IOP-lowering effect.

Accordingly, the need exists for new and better methods of lowering intra-ocular pressure, particularly in the treatment of one of the leading causes of blindness, glaucoma.

SUMMARY OF THE INVENTION

The present invention provides a method for reducing intra-ocular pressure using a new class of compounds hitherto used as high ceiling diuretics, also known as loop diuretics, due to their ability to completely inhibit sodium chloride transport in the thick ascending limb of the loop of Henle. It has been discovered that the trabecular meshwork cells of the mammalian eye regulate cell volume and fluid transport by means of a $Na^+$—$K^+$—$2Cl^-$ cotransporter mechanism, such as that found in the renal thick ascending limb of the loop of Henle. Compounds that substantially inhibit operation of this mechanism also increase the outflow of ocular fluids, thus lowering intra-ocular pressure. Such compounds are useful in treatment of diseases of the eye associated with elevated intra-ocular pressure, such as ocular hypertension and glaucoma.

Preferred compounds useful in the practice of this invention are furosemide, piretanide, benzmetanide, bumetanide, and torasernide, derivatives thereof with lipophilic and amphipathic characteristics designed to enhance penetration through the intact cornea, and pharmaceutically acceptable salts thereof. These outflow-increasing compounds are administered directly to the eye, either topically, by corneal iontophoresis, or by intracameral microinjection into the anterior chamber of the eye. The delivery of these compounds may be enhanced by the use of an erodible or sustained release ocular insert device. Lipophilic or amphipathic derivatives of these compounds are particularly preferred for topical administration.

A screening method is also provided to discover additional compounds with utility for lowering intra-ocular pressure by substantially inhibiting the $Na^+$—$K^+$—$2Cl^-$ cotransporter mechanism in trabecular meshwork cells.

A DETAILED DESCRIPTION OF THE INVENTION

Figure 1A:
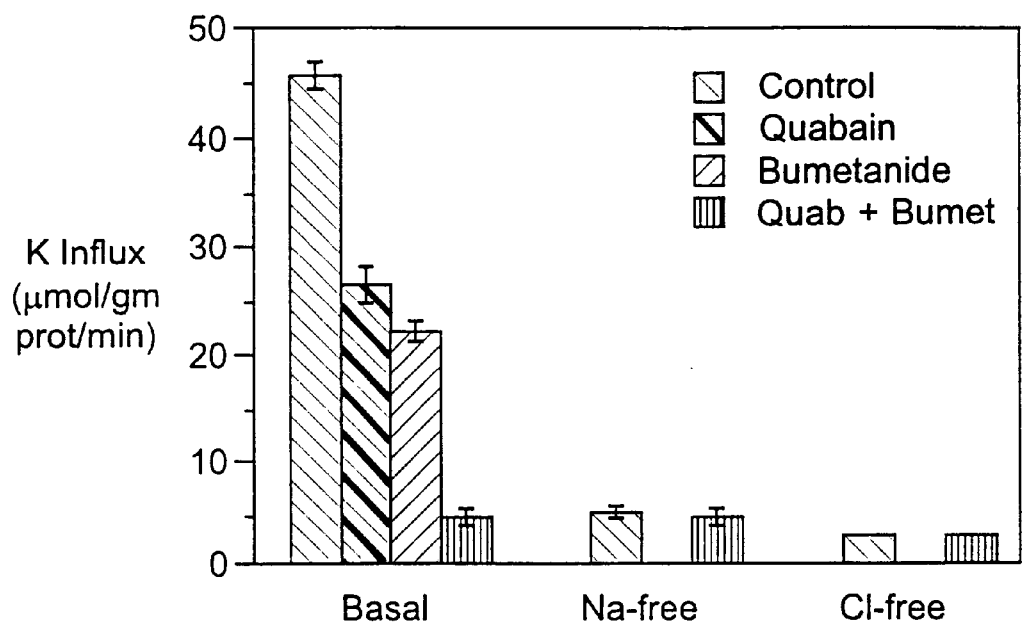
FIG. 1A is a bar graph comparing the rates of potassium influx in bovine trabecular meshwork (TM) cells preincubated and assayed in Hepes-buffered medium containing no drugs (control) or ouabain, bumetamide, or a combination of ouabain and bumetanide. $K^+$ influx was assessed $^{86}Rb$ influx (Rb quantitatively substitutes for K in this system) and the amount of radioactive contents was determined by liquid scintillation. Assay media were identical to preincubation media except that they also contained $^{86}Rb$ (1 $\mu$Ci/ml). Data represent mean values±SEM of quadruplicate determination from six experiments.

The present invention provides a method for increasing aqueous humor outflow in the eye of a human or other mammal by administration to the eye of an effective amount of a compound that substantially inhibits a $Na^+$—$K^+$—$2Cl^-$ cotransport mechanism, such as that found in the thick ascending limb of the loop of Henle. As used herein the. term "Na—K—Cl transporter" refers generically to the cotransporter systems, but does not specify the particular toichiometry of transport in the system described. On the other hand, as used herein the term $Na^+$—$K^+$—$2Cl^-$ cotransport system refers only to those cotransport systems having the indicated stoichiometry.

The output-increasing compound can be administered to the eye either topically or by intracameral microinjection into the anterior chamber of the eye, and is. therapeutically useful in reducing the intra-ocular pressure in prevention and/or treatment of diseases characterized by elevated intra-ocular pressure, such as ocular hypertension and glaucoma.

It has been discovered that mammalian trabecular meshwork (TM) cells, i.e., bovine and human, possess a prominent $Na^+$—$K^+$—$2Cl^-$ cotransport system comparable in activity to that observed in vascular endothelial cells and the one found in the thick ascending limb of the loop of Henle. Using bovine TM cells, we have found that hormones and neurotransmitters shown by others to modulate outflow through the trabecular meshwork also alter the activity of the cotransporter in these cells. The results of the present study indicate that in TM cells, $Na^+$—$K^+$—$2Cl^-$ cotransport activity is stimulated by vasopressin, elevation of intracellular Ca and activation of protein kinase C, and that the cotransporter is inhibited by elevation of intracellular cyclic AMP or cyclic GMP. Thus, agents that elevate cyclic nucleotides and increase aqueous outflow also inhibit Na—K—Cl cotransport activity, whereas agents that elevate Ca or activate protein kinase C and decrease aqueous outflow also stimulate $Na^+$—$K^+$—$2Cl^-$ cotransport activity of TM cells.

The inventors herein have employed a variety of drugs to increase aqueous outflow and thereby decrease intra-ocular pressure. Although ethacrynic acid was known to increase aqueous outflow in both monkey and human eye, the mechanism of its operation was unknown. The inventors herein have discovered that ethacrynic acid and a class of related drugs heretofore known to be useful as diuretics achieve their therapeutic effect in the eye by inhibition of a previously undiscovered $Na^+$—$K^+$—$2C^-$ cotransport system in bovine and human TM cells.

The Na—K—Cl cotransport in TM cells is stimulated by elevation of extracellular tonicity . Thus, TM cotransport is increased by cell shrinkage, as would be predicted if the cotransporter mediates a regulatory volume in crease in the TM cells. Exposure of TM cells to elevated extracellular tonicity has been found to cause an immediate cell shrinkage and a slower increase in cell volume that is blocked by bumetamide. These results indicate that TM cells do indeed regulate volume upon exposure to altered extracellular tonicity, and that they do so via a $Na^+$—$K^+$—$2C^-$ cotransport-dependent mechanism It has also been discovered that agonist- or drug-induced alteration of Na—K—Cl transporter activity in TM cells results in altered TM cell volume. Thus, accents, such as the phorbol ester PMA that stimulate the cotransporter also increase TM cell volume. By contrast agents such as bumetanide, ethacrynic acid, cyclic AMP, and cyclic GMP that inhibit cotransport, decrease TM cell volume. The cotransporter system is shown to be important for maintenance of TM cell volume even in the absence of a tonicity challenge. Thus, cell shrinkage induces elevated cotransport activity, consistent with a role for the transporter in regulatory volume increase, but at the same time a change in cotransport activity drives a change in TM cell volume. This is a strong indicator that the Na—K—Cl cotransporter is of central importance for regulation of TM cell volume by hormones and pharmacologic agents.

Alteration of Na—K—Cl cotransport activity and/or TM cell volume modulates permeability of the trabecular meshwork. It has been discovered that flux of $^{14}$C-sucrose across TM monolayers grown on filters was increased by exposure of the cells to bumetanide in a manner that continued to increase over the 15 minute assay period, indicating that bumetanide-induced decrease in TM cell volume causes an increase in monolayer permeability. Exposure of the TM cells to hypertonicity, which causes cell shrinkage, also causes an increase in permeability. As with endothelial cells, the hypertonicity-induced permeability increase in TM cells appears to be transient. These findings indicate that the Na—K—Cl cotransporter and intracellular volume control are determinants of barrier function in cultured TM cell monolayers.

Of greatest importance for the invention herein, these findings indicate that $Na^+$—$K^+$—$2Cl^-$ cotransport-mediated volume regulation of trabecular meshwork cells plays an important, perhaps central, role in maintaining and regulating barrier function, and as a result, the homeostatic outflow of aqueous humor facility in the eye. Abnormal function or regulation of this system plays a role in the pathophysiology of ocular hypertension and glaucoma.

Abnormal function of the $Na^+$—$K^+$— $2Cl^-$ cotransporter in the eye can be modulated by administration directly to the eye of compounds that increase or decrease the biological activity of the Na—K—Cl cotransporter system in the TM cells. In treatment of ocular hypertension and glaucoma, wherein the pressure of the ocular fluid is undesirably elevated, compounds are administered directly to the eye that substantially inhibit activity of the $Na^+$—$K^+$—$Cl^{-2}$ cotransporter, and hence increase outflow of aqueous humor from the eye.

The in vivo biological activity of outflow-increasing compounds useful in the practice of this invention for increasing outflow of intra-ocular humor from the eye can be predicted using the well known in vitro test for determining compounds that inhibit the $Na^+$—$K^+$—$Cl^{-2}$ co-transporter of rabbit renal thick ascending limb of the loop of Henle, as described by M. B. Burg et al. (*Am J. Physiol.* 210:1293–1298, 1966) as modified by R. Greger (*Pflüger's Arch.* 390:30–37, 1981) and R. Greger et al. (*Pflüger's Arch.* 389:175–176, 1981), both of which are incorporated herein by reference in their entireties. In brief, this in vitro test uses the Na+2Cl$^-$K$^+$ co-transporter system found in the cortical thick ascending limbs of the loop of Henle of mammals, particularly rabbits, for example, female white New Zealand rabbits. The tubules are dissected and perfused according to the known techniques, but with the rate of perfusion through the lumen kept high (10–20 nl/min) to prevent changes in the ionic composition of the perfusate along the perfused tubule. As control perfusate, a solution containing (mM): NaCl 145; K$_2$HPO$_4$ 1.6; KH$_2$PO$_4$ 0.4; MgCl$_2$ 1; Ca gluconate 1.3; and glucose 5 is used on both sides of the epithelium with pH adjusted to 7.4

The transepithelial potential ($V_{te}$) is recorded continuously on both ends of the tubule. The specific transepithelial resistance ($R_{te}$) is calculated from the input resistance obtained by the injection of short current pulses (25–30 Na, 800 ms) into the tubule lumen. The ratio of both values ($V_{te}R_{te}$) gives the equivalent short circuit current $I_{te}$. There is a direct relationship between the decrease of $I_{te}$ and the inhibition of the $Na^+2Cl^-K^+$ co-transporter by contact with the test compound (R. Greger et al, *Klin. Wochenschr.* 61:1019–1027, 1983). For each drug under study, dose-response curves are established by adding compounds at various concentrations to the luminal perfusate with at least three determinations for each concentration. These response curves are then used to calculate the concentration necessary to block 50% of the short circuit current (IC50). Compounds with therapeutic utility usefull for increasing the outflow of aqueous humor from the eye, for instance in treatment of glaucoma, are characterized by having an IC50 at or below those of bumetanide or torasemide, or about 0.30 $\mu$m. To be useful in clinically enhancing aqueous humor outflow, compounds shown by this screening method to inhibit Na—K—Cl cotransport may also be screened for their activity in animal or human TM cells by testing their ability to inhibit Na—K—Cl cotransport in in vitro tissue culture. In this in vitro assay of pharmacologic activity, Na—K—Cl cotransport may be measured in these cells as ouabain-insensitive, bumetenide-sensitive potassium influx, using a radionuclide, such as $^{86}$Rb, as a tracer for potassium. For usefulness in the practice of this invention, it is preferred that the outflow increasing composition inhibit ouabain-insensitive, bumetenide-sensitive potassium influx in human or bovine TM cells by at least 50%. Details of this method have been published previously in M. E. O'Donnell, *J. Biol. Chem.* 264: 11559–11566, 1991, which is incorporated herein by reference in its entirety. An illustration of the use of this method is found in Example 1B of this application.

Compounds to be administered to the eye topically in the practice of this invention must not only inhibit $Na^+$—$K^+$—$Cl^{-2}$ cotransporter system, but must also be sufficiently lipophilic to penetrate the corneal membrane. The lipophilicity of a compound is expressed in terms of an octanol-:water coefficient, determined by tile standard technique of radiolabelling the compound and introducing a small amount into equal volumes of octanol and tris buffer (50 mM, pH 7.4). Generally the lipophilicity (log P') is expressed as the logarithm of the partition coefficient in n-octanol/phosphate buffer, pH 7.4 using the well known shake-flask method as described by Cloux, et al., *J. Pharm. Belg.*, 43:141–151, 1973, which is incorporated herein by reference in its entirety. The coefficient of lipophilicity (log P') of the compounds useful for topical application to decrease intra-ocular pressure is preferably at least 0.005, and more preferably at least 0.01.

The lipophilicity of the aqueous humor outflow-increasing compounds of this invention can also be determined using a reversed phase, high performance liquid chromatograph (RP-HPLC) system for determination of the log P' of the drug as described in B. Masereel, et al. (*J. Pharm. Pharmacol.* 44:589–593, 1992), which is incorporated herein by reference in its entirety. Briefly, a reversed phase column (RP-18) is equilibrated with n-propanol/phosphate buffer, pH 7.4 at a ratio of 30:70). Compounds to be tested are dissolved and eluted with the same solution. A series of standards with a wide range of lipophilicity, as determined by the shake-flask method, is run and a calibration curve is established for each session. KNO$_3$ is injected to determine the void volume, and log$_r$ K$_0$'=log(t$_0$-t)/t is determined, wherein $t_r$ is the drug retention time and $t_0$ is the retention time of $NO_3$—. Calibration curves are calculated using log P' and log k' values. Log P' values of other compounds are obtained by interpolation of the standard curves.

Among the preferred outflow-increasing compounds of this invention are lipophilic derivatives of torasemide, and biologically compatible salts thereof, which are potent blockers of the $Na^+2Cl^-K^+$ co-transporter in the thick ascending limb of the loop of Henle (J. Delarge, *Arzneim. Forsch.* 38:144–150, 1988). These compounds combine a high degree of lipophilicity and biological activity. The chemical structure of torasernide (also known as Demodex™ and torsemide) is represented by the following formula:

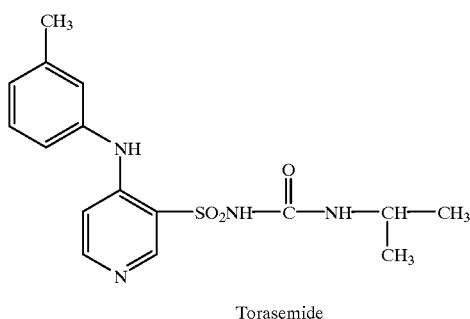

Torasemide

The chemical structures of the lipophilic derivatives of torasernide are represented by the following general formula:

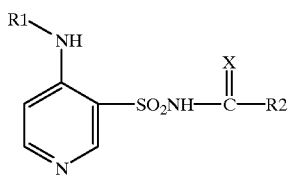

wherein $R^1$ is selected from the group consisting of 3-methyl benzyl and 6–12 membered substituted or unsubstitued cycloalkyls, preferably an unsubstituted cyclo-octyl or a m-substituted phenyl, where the substituent is selected from —$CH_3$, —$CF_3$, or —Cl; and further wherein $R^2$ is selected from the group consisting of aminoisopropyl, 6–8 membered aminocycloalkyls and perhydroazepine. As shown by the data in Table 1 below, an increase of the number of methylenes of the $R^1$ cycloalkyl group increases the inhibitory potency (compounds 9–11, 12–14, 15–17, and 21–23), whatever the size of $R^2$, but a cyclododecyl moiety in this position results in an inactive compound (compound 18). Incorporation of the distal nitrogen of the sulphonylurea moiety into a saturated ring leads to very active molecules (compounds 21–24). And a piperidine ring in the $R^2$ position (compound 22) increases inhibition potency compared with perhydroazepine (compound 24). Comparison of the log P' with the number of carbons in $R^1+R^2$ for each cycloalkyl disubstituted compound indicates that an increase of one methylene results in an enhanced lipophilicity of some 0.35 log units. Moreover, there is a correlation between log P' and inhibition potency.

TABLE 1

| Compound | $N^{13}$ R1 | R2 | X | log P* | IC50 |
|---|---|---|---|---|---|
| 7 | 3-methylbenzyl | isopropyl-NH— | O | +0.45 | 0.30 |
| 8 | cyclohexyl | isopropyl-NH— | O | +0.58 | 0.70 |
| 9 | cyclohexyl | cyclohexyl-NH— | O | +1.33 | 19 |
| 10 | cycloheptyl | cyclohexyl-NH— | O | +1.57 | 3.5 |
| 11 | cyclooctyl | cyclohexyl-NH— | O | +2.06 | 0.47 |

TABLE 1-continued
| Compound | N¹³ R1 | R2 | X | log P* | IC50 |
|---|---|---|---|---|---|
| 12 | 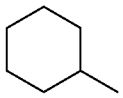 | 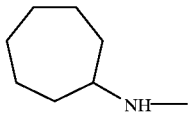 | O | +1.72 | 9.6 |
| 13 | 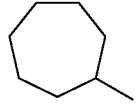 | 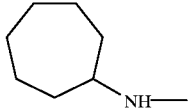 | O | +2.06 | 2.8 |
| 14 | 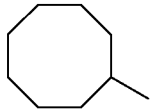 | 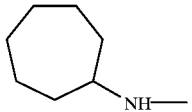 | O | +2.45 | 2.0 |
| 15 | 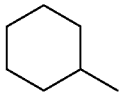 | 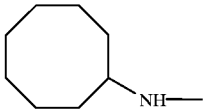 | O | +2.07 | 14 |
| 16 | 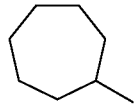 | 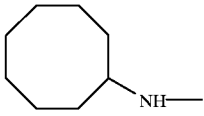 | O | +2.44 | 1.7 |
| 17 | 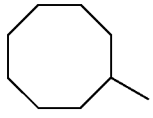 | 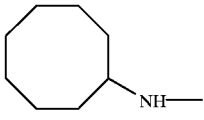 | O | +2.70 | 0.56 |
| 18 | 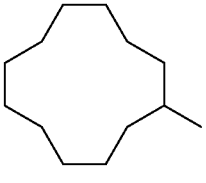 | 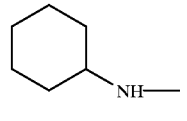 | O | +3.45 | >100 |
| 19 | 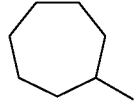 | 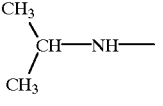 | S | +0.96 | 1.3 |
| 20 | 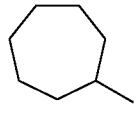 | 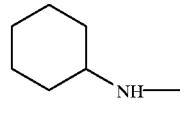 | S | +1.79 | 0.79 |

TABLE 1-continued

| Compound | N$^{13}$ R1 | R2 | X | log P* | IC50 |
|---|---|---|---|---|---|
| 21 | cyclohexyl-CH | piperidinyl | O | +0.62 | 0.82 |
| 22 | cycloheptyl-CH | piperidinyl | O | +1.24 | 0.25 |
| 23 | cyclooctyl-CH | piperidinyl | O | +1.65 | 0.15 |
| 24 | cycloheptyl-CH | azepanyl | O | +1.53 | 0.80 |
| 25 | furfuryl-CH$_2$-NH-(substituted benzene with COOH, Cl, SO$_2$NH$_2$) | | | −0.92 | 3.0 |

Methods of synthesis of torasernide and of the lipophilic torasemide derivatives of this invention are well known in the art, particularly as disclosed in B. Masereel et al., *J. Pharm. Pharmacol.* 44:589–593, 1992, which is incorporated herein in its entirety, and in U.S. Pat. No. 4,861,786 to Demmer et al., which is incorporated herein in its entirety.

Additional compounds useful in the practice of this invention are a class of high ceiling diuretics, also known as loop diuretics, due to their ability to completely inhibit sodium chloride transport in the thick ascending limb of the loop of Henle at luminal concentrations of the drug in the range expected to occur in vivo. These drugs act at the luminal face of the epithelial cells to inhibit the Na$^+$—K$^+$—2Cl$^-$ cotransport mechanism (*Goodman and Gilman's The Pharmacological Basis of Therapeutics*, 8th Ed., A. G. Gilman et al., Ed., Pergarnon Press, New York, Elmsforth, N.Y., 1990, page 722).

Because these drugs inhibit the cotransport mechanism discovered by the inventors herein to operate in TM cells in the mammalian eye, all drugs of this class of diuretics are also useful for increasing outflow of aqueous humor from the eye when administered as disclosed herein. Hence, they are useful therapeutics for treatment of glaucoma and other conditions attributable to unnaturally high intra-ocular pressure. Three drugs of this class, whose chemical structures are shown in Table 2 below, are in clinical use in the United States as diuretics: ethacrynic acid, furosemide, and bumetanide. A number of other compounds in this class, including benzmetanide and piretanide, some of which are in used in other countries, are described in R. Greger and P. Wangemann, "Loop Diuretics," *Renal Physiology* 10:174–183, 1987, which is incorporated herein by reference in its entirety. It is also contemplated that derivatives of these compounds, as well as other compounds, can be used in the practice of this invention shown to inhibit the Na$^-$—K$^-$—2Cl$^-$ cotransport mechanism by the thick ascending limb screening test and the in vitro assay of cotransport activity and inhibition in cultured TM cells taught herein.

TABLE 2

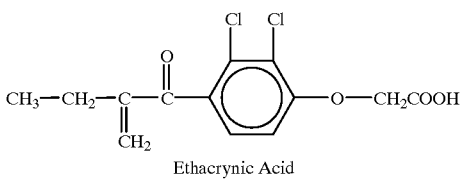

Ethacrynic Acid

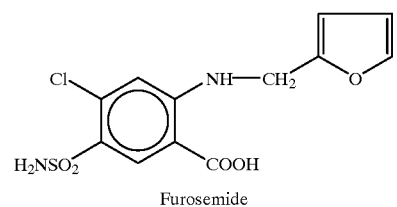

Furosemide

TABLE 2-continued

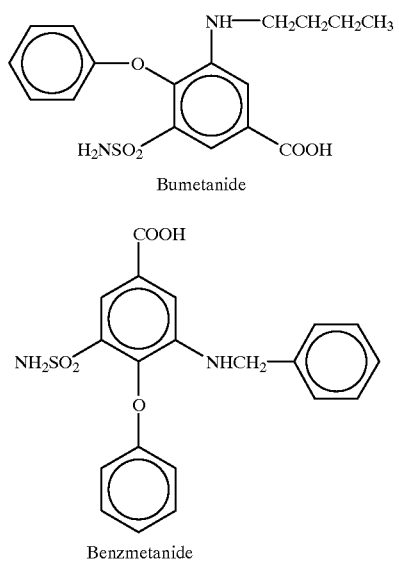

Bumetanide

Benzmetanide

In two extensive studies (E. Schlatter et al, *Pflügers Arch.* 405:367–376, 1985 and M. Wittner et al., *Pfügers Arch.* 408:54–62, 1987) the structure-activity relationships of furosemide analogues and torasernide analogues have been examined, and general conclusions have been drawn regarding the minimum requirements needed for reversible interaction with the $Na^+$—$K^+$—$2Cl^-$ carrier. These requirements can be summarized as follows: (1) an anionic group is mandatory—this group can be a tetrazolate, a sulfonate, a carboxylate, or a sulfonyl urea; (2) in ortho or meta position to the anionic group, a secondary (e.g., furosermide) or a tertiary (e.g. piretanide) amine is needed; (3) this amino group links the anionic moiety to an apolar residue, and (4) in meta position to the anionic group, a sulfonamide group (e.g. piretanide) or a pyridino nitrogen (e.g., torasemide) is necessary (R. Weger, et al., supra, p. 179).

The outflow-increasing compounds disclosed herein, which inhibit the $Na^+$—$K^+$—$2Cl^-$ cotransport mechanism, can be administered either topically or by microinjection into the trabecular meshwork. For topical administration, the compound is dissolved in a pharmaceutically acceptable carrier substance, e.g., physiological saline. Additional pharmaceutically acceptable carrier substances can readily be supplied by one skilled in the art. For compounds having limited water solubility, the liquid carrier medium can contain an organic solvent, for example, 3% methyl cellulose. Methyl cellulose provides, by its high viscosity, increased contact time between the compound and the surface of the eye, and therefore increases corneal penetration. Corneal penetration can also be increased by administering the compound mixed with an agent that slightly disrupts the corneal membrane, for example 0.025% benzalkonium chloride, which also serves as a bacteriostatic preservative in various commercial formulations). Corneal penetration may also be increased by delivering a suspension of liposomes that incorporate the therapeutic compound, as described by Davies et al. ("Advanced Corneal Delivery Systems: Liposomes" in *Opthalmic Drug Delivery Systems*, A. K. Mitra, Ed., Vol. 58, pages 289–306 in the series *Drugs and the Pharmaceutical Sciences*, 1993, Marcel Dekker, Inc., New York. The outflow-increasing compound is administered periodically (for example, one time per week to ten times per day). Administration is by applying drops of the compound in solution using an eye dropper, such that an effective amount of the compound is delivered through the cornea to the trabecular meshwork. Administration may also be by a sustained-release formulation, such as a liposome, or via an ocular insert designed to enhance the dwelling time of the compound in the tear film and improve patient compliance with therapy, such as those described by R. Bawa, in A. K. Mitra, Ed., supra, Chapter 11, pages 223–260.

The "effective amount" of the compound to be delivered in one administration will depend on individual patient characteristics, e.g. the severity of the disease, as well as the characteristics of the administered compound, such as its lipophilicity and biological activity in stimulating the $Na^+$—$K^+$—$Cl^{-2}$ cotransporter system in TM cells. Generally, an "effective amount" is that amount necessary to substantially inhibit the $Na^+$—$K^+$—$Cl^{-2}$ cotransporter mechanism or establish homeostasis of the aqueous fluid in the eye as indicated by the intra-ocular pressure. Intra-ocular pressure reflects the balance between the production and outflow of aqueous humor, and the normal range is 2.09±0.33 kPa (15.8±2.5 mmHg) as measured by applanation tonometry (by planating the corneal surface) (*Harrison's Principles of Internal Medicine*, 13th Ed., Isselbacher et al., Ed., McGraw Hill, Inc., New York, p. 105). Typically, each drop contains 50–100 microliters of a 5–10 miM solution of the compound, so that 0.025 to 0.10 moles of the compound are delivered to each eye per day. Systemic absorption of the drug can be minimized by digital compression of the inner canthus of the eye during and for a short time following its instillation into the eye.

Direct microinjection of the solubilized compound to a site near the trabecular meshwork offers the advantage of concentrating the compound in the location where it is needed, while avoiding the possibility of side effects resulting from generalized exposure of the eye to the compound. Microinjection may also provide the advantage of permitting infrequent periodic administration, for example every few weeks, months, or even years, in contrast to the more frequent administrations required in the case of topical administration. Also, direct microinjection may promote the washing out of the trabecular meshwork of extracellular material interfering with fluid outflow. Preferably microinjection is administered via subconjunctival injection, most preferably into the superior aspect of the globe at the 12:00 o'clock position, from which point the drug reaches the intra-ocular space by diffusing passively across the scleral fibers, which offer essentially no barrier to penetration. Dosage for microinjection, like that for topical administration, vanes with the above-mentioned parameters. Typically, microinjection dosage is such that a final concentration of the compound within the trabecular meshwork of 0.01 to 1.0 mM is reached.

The following examples illustrate the manner in which the invention can be practiced. It is understood, however, that the examples are for the purpose of illustration and the invention is not to be regarded as limited to any of the specific materials or conditions therein.

EXAMPLE 1

A. Cell Culture

Bovine trabecular meshwork (TM) cells (Department of Ophthalmology, Lions of Illinois Eye Research Institute, Chicago, Ill.) and human trabecular meshwork isolated by methods based on those of Polansky et al. (*Invest. Ophthal-* mol. Vis. Sci., 18:10 43–1049, 1979). Briefly, for isolation of bovine TM cells, eyes from healthy, freshly slaughtered young cows were enucleated. The TM was surgically excised, taking care not to include surrounding tissues. Explants were cut into small pieces (~1 mm$^3$), put in collagen-coated 175cm$^2$ tissue culture flasks without medium for 1 minute until adhering, then growth medium was added to the flask. The media used was Eagle's minimal essential medium (MEM) supplemented with 10% fetal bovine serum (Hyclone Laboratories, Logan, Utah), essential and non-essential amino acids, glutamine, and penicillin/streptomycin. The explants were maintained in a humidified $CO_2$ incubator at 37° C. and 5% $CO_2$. When cells growing out of the explant reached confluence, they were trypsinized and subcultured. Cultures that appeared to contain non-trabecular meshwork cells were discarded. Cultures were maintained by refeeding every 2 days and splitting weekly.

Similar techniques were used in isolation of human TM cells, except that human TM derived from three sources: 1) research donor eyes (presumed to be normal) from the eye bank of the University of California, Davis Medical Center; 2) otherwise healthy eyes enucleated because of life-threatening malignancies in the posterior pole (e.g., retinoblastoma or choroidal melanoma); and 3) trabeculectomy specimens. At the time of trabeculectomy surgery, the surgeon created a partial thickness scleral flap, unroofing the TM at the surgical lirnbus. A small piece ($\approx$1 to 2 mm$^3$) was then excised to create the surgical fistula.

Both types of TM cells were maintained in collagen-coated tissue culture flasks and were used between passages 8 and 12 for bovine and between passages 3 and 8 for human. For experiments, cells were removed from the flasks by brief typsinization and were subcultured onto 24 well plates coated with collagen Type I (Collaborative Research, Inc., Bedford, Mass.) for radioisotopic transport and cell volume experiments or onto collagen-coated tissue culture filter inserts (Biocoat™, 13 mm diameter, 0.45 $\mu$m pore size (Collaborative Research Inc.). Cells were used 5–7 days later as confluent monolayers and growth medium was replaced every 2 days.

B. Transport Measurements

Agents known to increase aqueous outflow should inhibit activity of the cotransporter, and agents which decrease aqueous outflow should stimulate the cotransporter. Further these agents should alter $Na^+$—$K^+$—$2Cl^-$ cotransport with a potency similar to that observed for their actions on trabecular meshwork function.

Na—K—Cl cotransport was measured as ouabain-insensitive, bumetanide-sensitive potassium influx, using $^{86}$Rb as a tracer for potassium. Details of this method have been published previously (O'Donnell, M. E., supra, 1989). Briefly, bovine or human TM cell monolayers on 24 well plates were equilibrated for 10 minutes at 37° C. in a Hepes-buffered minimal essential medium (MEM) containing (in mM): 144 Na, 147 Cl, 5.8 K, 1.2 Ca, 4.2 $HCO_3$, 0.4 $HPO_4$, 0.4 $H_2PO_4$, 0.4 $SO_4$, 5.6 glucose and 20 Hepes. The cells were then preincubated and assayed for 5 minutes each with Hepes-buffered MEM containing 1 or 0 mM ouabain (Boehringer-Mannheim Biochemicals, Indianapolis, Ind.), 10 or 0 $\mu$M bumetanide (Hoffman-LaRoche, Nutley, N.J.) and either 145 or 0 mM Na and Cl (Na isosmotically replaced by choline, Cl isosmotically replaced by gluconate). The assay medium also contained $^{86}$Rb (1 $\mu$Ci/ml) (Dupont New England Nuclear, Boston, Mass.). The assay was terminated by rinsing the wells with ice-cold isotonic $MgCl_2$, then extracting the contents with 0.2% sodium dodecyl sulfate (SDS), and determining the amount of radioactive contents by liquid scintillation. Osmolarities of all preincubation and assay media were verified by osmometry (Model 3W2, Advanced Instruments, Norwood, Mass.).

Figure 1B:
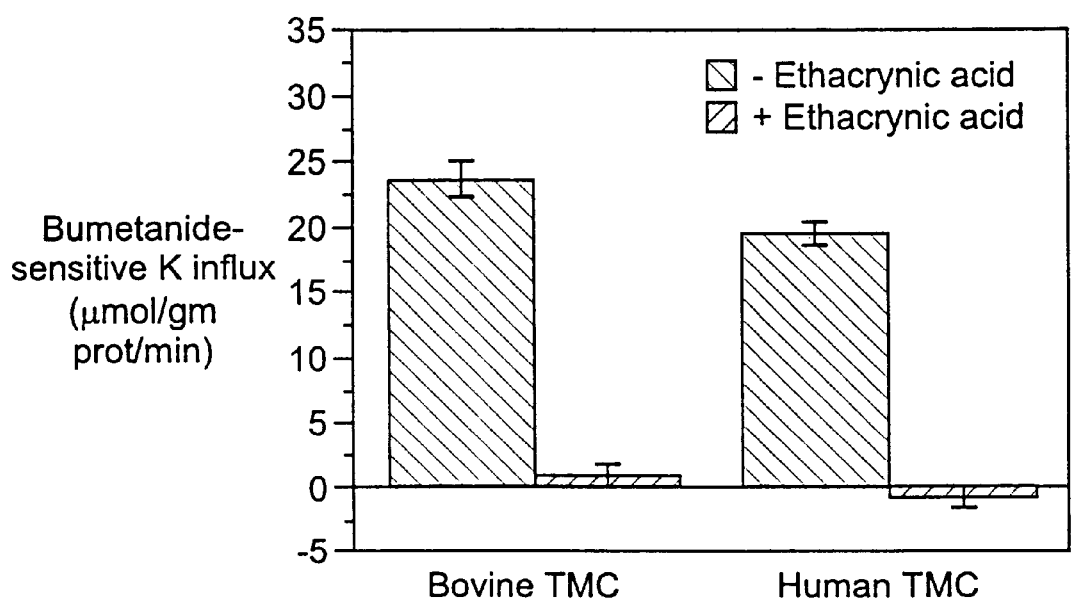
FIG. 1B is a bar graph comparing bumetanide-sensitive potassium influx of bovine and human TM cells, evaluated in the presence or absence of ethacrynic acid (1 mM). Data represent means±SEM of quadruplicate determinations from six and two experiments (bovine and human TM cells, respectively).

Evaluation of K influx in cultured trabecular meshwork cells revealed the presence of a robust $Na^+$—$K^+$—$2Cl^-$ cotransport system. As shown in FIGS. 1A and 1B, bovine TM cells exhibited a total K uptake of 49±1.47 $\mu$mol K/gm protein/min. The K influx was decreased by 10 $\mu$M bumetanide to 22.09±1.14 $\mu$mol K/gm protein/min. and by 1 mM ouabain to 24.16±1.36 $\mu$mol K/gm protein/min, indicating the presence of both Na/K pump activity and $Na^+$—$K^+$—$Cl^{-2}$ cotransport activity. A bumetanide-sensitive K influx was also observed in the presence of ouabain. Thus, high levels of bumetanide-sensitive K influx are present in these cells, whether measured with or without Na/K pump inhibition, namely 20.1 and 26.9 $\mu$mol K/gm protein/min, respectively.

Removal of either Na or Cl from the assay media abolished bumetanide-sensitive K influx of the trabecular meshwork cells, indicating an obligate presence of Na and Cl for the bumetanide-sensitive K influx to occur, as is required in Na—K—Cl cotransport activity.

In the bovine TM cells, cotransport-mediated K influx was approximately 55% of the total influx, compared to 50% of Na/K pump-mediated K influx. This result shows that the cotransporter provides a substantial contribution to TM cell function. Half-maximal inhibition of K influx was observed with 0.1 $\mu$M bumetanide, whether in the presence or absence of ouabain. This potency is similar to that reported for a number of other cell types, including vascular endothelial cells (Chipperfield, A., supra; O'Donnell, M. E., supra, 1989; O'Grady, et al., supra). As shown in FIG. 1B, high magnitude bumetanide-sensitive K influxes were observed in human as well as in bovine TM cells.

Previous studies of other cell types have shown that ethacrynic acid, structurally distinct from bumetanide, also inhibits $Na^+$—$K^+$—$2Cl^-$ cotransport activity (Palfrey, et al., supra). If exposure of TM cells to ethacrynic acid inhibits $Na^+$—$K^+$—$2Cl^-$ cotransport activity, then it should decrease or abolish the bumetanide-sensitive portion of K influx in these cells. As shown by the results summarized in FIG. 1B, bumetarude-sensitive K influx of both bovine and human TM cells was abolished in the presence of 1 mM ethacrynic acid.

In order to determine whether activity of the cotransporter is responsible for mediating net ion uptake, it is necessary to evaluate the influence of cotransport activity on cell ion content. Thus, studies were conducted to determine the magnitude of net K uptake mediated by the TM cell $Na^+$—$K^+$—$2Cl^-$ cotransporter. For determination of the net potassium uptake, the potassium contents of TM cells were evaluated by atomic absorption spectrophotometry, as described previously by O'Donnell, M. E. (supra, 1993). Briefly, cells were preincubated in 10 $\mu$M bumetanide for 5 minutes, and assayed as described above, with the exception that no $^{86}$Rb was present during the assay. Cell ionic contents were extracted with 5% trichloroacetic acid following removal of extracellular potassium by washing the monolayers with ice-cold 0.1 M $MgCl_2$.

Under steady state conditions, $Na^+$—$K^+$—$2Cl^-$ cotransport mediated a net uptake of K such that inhibition of the cotransporter results in a decrease in cell K (via other transport pathways). This bumetanide-sensitive net K uptake was found to be 7.78±1.98 μmol K/gm protein/nin. If either Na or Cl was omitted from the incubation medium, the bumetanide-sensitive net K uptake was abolished (1.71±2.49 and −2.62±2.82 μmol K/gm protein/min, respectively, n=8).

C. Measurements of Cell Volume

If Na—K—Cl cotransport of TM cells is important for regulation and maintenance of cell volume, then alteration of cotransport activity should lead to altered intracellular cell volume. Omission of either Na, K or Cl from the assay medium should also cause a decrease in cell volume because the Na—K—Cl cotransporter cannot operate if any one of the transported ion species is absent from the extracellular medium. In addition, second messengers (e.g., cyclic AMP and cyclic GMP), as well as hormones and neurotransmitters found to be inhibitory to cotransport should cause a decrease in trabecular meshwork cell volume. Similarly, second messengers (e.g., Ca and protein kinase C) identified to be stimulatory to cotransport activity should cause an increase in trabecular meshwork cell volume, as should hormones and neurotransmitters identified to stimulate the cotransporter. Further, if Na—K—Cl cotransport is responsible for mediating hormone-, neurotransmitter- and second messenger-induced increases in cell volume, then blocking cotransport activity by bumetanide should prevent the elevation of cell volume induced by these agents. In addition, the potency with which each of these agents alters Na—K—Cl cotransport activity should be similar to the potency for alteration of intracellular volume.

The intracellular volume of human and bovine TM cells was evaluated by two methods: 1) radioisotopic evaluation of TM monolayer intracellular water space using $^{14}$C-urea and $^{14}$C-sucrose as markers of total and extracellular space, respectively; and 2) electronic cell sizing of suspended TM cells, using a Coulter Counter™ assay (Coulter Electronics, Ltd., Hialeah, Fla.). Details of these methods have been described previously by O'Donnell (O'Donnell, M. E., supra, 1993).

Figure 2A:
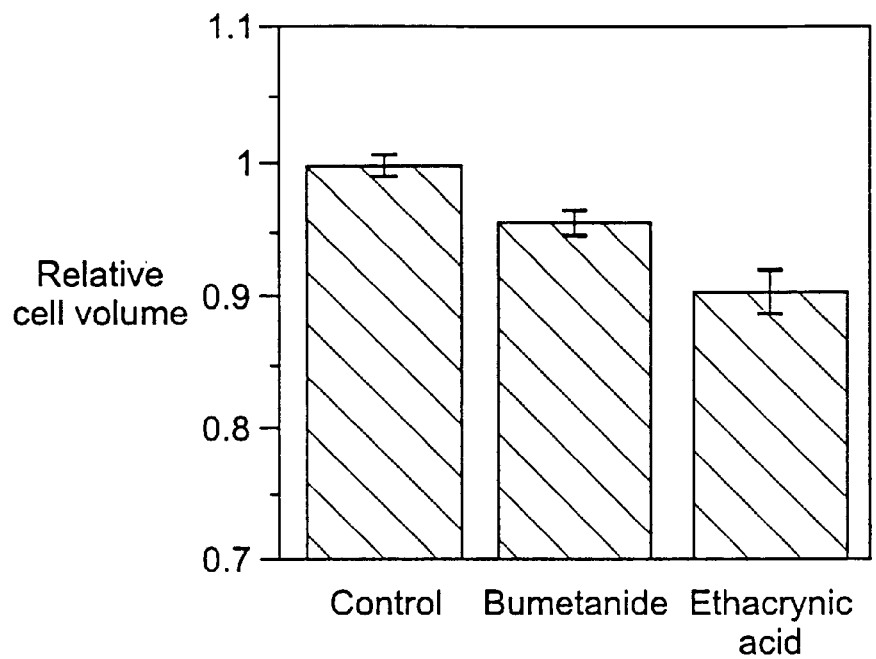
FIG. 2A is a bar graph comparing the absolute cell volumes of bovine TM cells evaluated by electronic cell sizing following 30 minute exposure to bumetanide (0 or 10 μM) or ethacrynic acid (0 or 1 mM). Data are mean values±SEM, n=3.

By the first method, cell monolayers were preequilibrated for 30 minutes in Hepes MEM at 37° C. in an air atmosphere, then incubated for 20 minutes in Hepes MEM containing 0 or 10 μM bumetanide, ethacrynic acid, or other agents to be tested, and finally incubated for 10 minutes in the same medium containing either $^4$C-urea or $^{14}$C-sucrose (both at 1 μCi/ml). Monolayers were then rinsed with isotonic ice-cold MgCl$_2$ and radioactivity of SDS extracts determined by liquid scintillation. Specific activities (counts per minute/ml) of $^{14}$C-urea and $^{14}$C-sucrose in the assay medium were determined and used to calculate water space associated with trapped radioactivity (expressed as μl/mg protein. Intracellular volume was calculated as the difference between the water space determined for $^{14}$C-urea (a marker for intracellular plus trapped extracellular space) and $^{14}$C-sucrose (a marker for trapped extracellular space). FIG. 2A shows that when the volume of the cells was assessed by electronic cell sizing of cell suspensions, exposure of the cells to either bumetanide or ethacrynic acid caused significant reduction of intracellular volume as compared to exposure to the Hepes MEM control.

By the second method, TM cells were trypsinized briefly in Ca-free medium, then rinsed with medium containing trypsin inhibitor and suspended in Hepes MEM. Mean cell volumes were then analyzed by electronic cell sizing on a Coulter Counter™ radioassay (Model ZM). with channelizer (C256), using at least 50,000 cells per data point and an orifice diameter of 140 μm. Aliquots of suspended cells were diluted into Hepes MEM containing the tonicity and/or agents to be evaluated. Mean cell volumes of each suspension aliquot were followed over time, starting at 1 minute after addition of cells to the assay media. Cell suspensions were maintained at 37° C. throughout the assay period. Absolute volumes (picoliters/cell) were calculated from distribution curves of cell diameter, using a standard curve generated by polystyrene latex beads of known diameter.

Figure 2B:
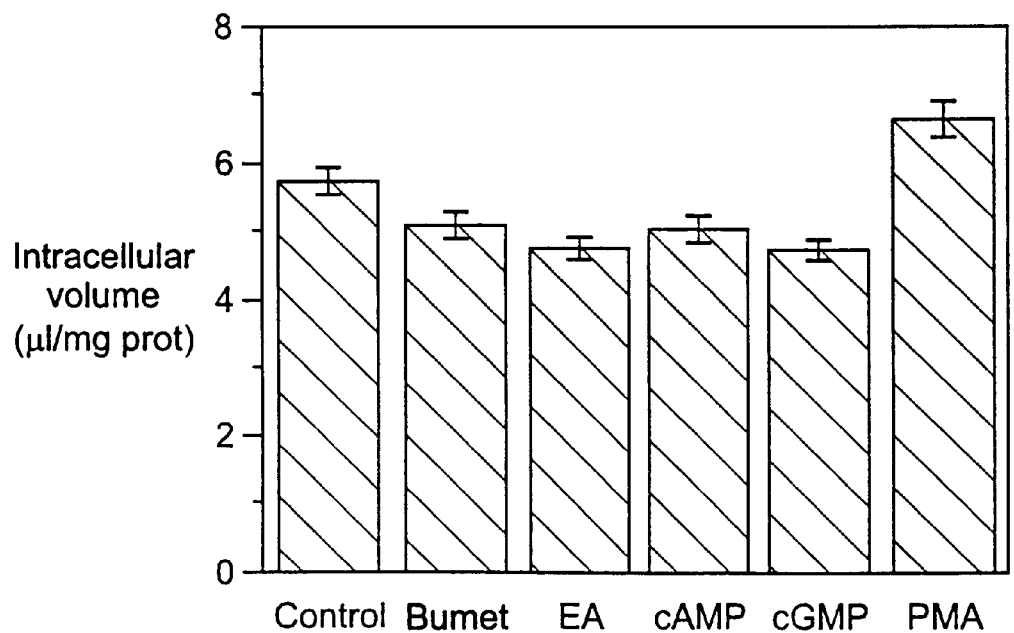
FIG. 2B is a bar graph comparing the relative cell volumes of bovine TM cells as evaluated by radioisotopic determination of intracellular water space. Confluent trabecular meshwork cell monolayers were preincubated in media containing bumetanide (0 or 10 μM), ethacrynic acid (0 or 1 mM), 8-bromo-cyclic AMP (50 μM), 8-bromo-cyclic GMP (50 μM), or PMA (50 nM), and also containing either $^{14}$C-urea or $^{14}$C-sucrose. Specific activities of the radioactively tagged agents were used to calculate water space associated with total and residual extracellular radioactivity, respectively. Data are means±SEM, n=8.

If hormones and neurotransmitters alter activity of $Na^+$—$K^+$—$2Cl^-$ cotransport, second messengers reported to be elevated in trabecular meshwork cells by these agents should also modulate activity of the cotransporter. Thus, experiments were conducted to evaluate the effect on activity of the cotransporter of altering intracellular second messenger levels The effects of 20 minute exposures of cyclic AMP, cyclic GMP and the phorbol ester PMA on TM cell volume are also shown in FIG. 2B. Consistent with their effects on $Na^+$—$K^+$—$2Cl^-$ cotransport activity, both cyclic nucleotides reduced TM cell volume while the phorbol ester PMA increased cell volume. These findings are consistent with the hypothesis that alteration of $Na^+$—$K^+$—$2Cl^-$ cotransport activity by hormones, neurotransmitters and drugs can cause alteration of TM cell volume.

D. Permeability Measurements

A role for $Na^+$—$K^+$—$2Cl^-$ cotransport in regulation of trabecular meshwork cell volume requires that changes in activity of the cotransporter result in net changes in cell content of Na, K and/or Cl. If the cotransporter is involved in maintaining intracellular volume under steady state conditions, then inhibiting activity of the cotransporter should cause a decrease in Na, K and/or Cl content of the cells, which would then cause a loss of water from the cells and shrinkage.

To investigate the possibility that alteration of TM intracellular volume results in modulation of trabecular meshwork barrier permeability, we evaluated the flux of $^{14}$C-sucrose across confluent TM cell monolayers grown on permeable filters. Cells were grown to confluence on collagen-coated dual level tissue culture filter inserts placed in covered multiwell cluster plates, as shown schematically in FIG. 3A, wherein lower chamber 2 is formed by suspension of membrane 4 with cells attached into holder 6, which is covered by cover 8. Upper chamber 10 is formed by the space within the holder above the membrane. Growth media (EMEM) volumes of 0.5 and 1.5 ml were used for upper and lower chambers, respectively, as previously described (Kajimura, et Al, *FASEB J*., 8:A1045, 1994) for evaluation of endothelial cell monolayers and for evaluation of water permeability of TM cell monolayers (Perkins, et al, *Invest. OphthalmoL Vis. Sci*., 29:1836–1846, 1988). One insert was placed in each of 12 wells in a cluster plate. Permeability was assessed as the flux of $^{14}$C-sucrose across the TM cell monolayers. Both upper and lower chambers of the multiwell cluster plates were equilibrated for 30 minutes in Hepes MEM at 37° C. in a gyrotary water bath, shaking at 60 cycles per minute, to ensure adequate mixing. Aliquots of medium were sampled at various times from the lower chamber to determine sucrose content. The sample volume removed was replaced each time with an equal volume of isotonic or hypertonic sucrose-free medium. Sucrose content of the samples was determined by spectrofluorometric methods. The amount of solute was calculated from the radioactivity present in the sample and the specific activity (cpm/μmol) of the $^{14}$C-sucrose.

Figure 4:
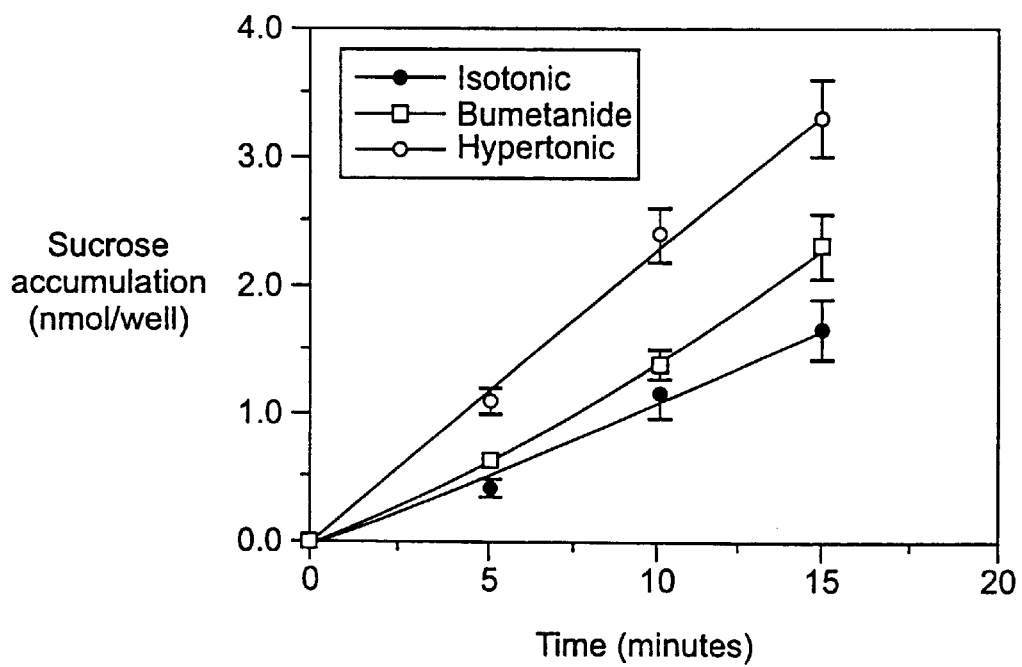
FIG. 4 is a graph comparing the effects of isotonic medium (—●—), hypertonic medium (—○—), and bumetanide (—□—) on permeability of trabecular meshwork cell monolayers grown on tissue culture filter inserts. The upper chamber also contained 1 μCi/ml $^{14}$C-sucrose. Aliquots were removed from the lower chamber at times indicated and evaluated for radioactivity to quantitate sucrose. Data represent mean values±SEM of six replicates from a representative experiment.

As shown in FIG. 4, shrinkage of TM cells by exposure to hypertonic medium caused an elevation of monolayer permeability to sucrose above that observed with isotonic medium. Permeability was also increased by bumetanide, with the rate of sucrose accumulation increasing over the 15 minute assay period, consistent with our finding that bunetamide causes reduction of TM cell volume.

E. Statistical Analysis

Experimental results were analyzed by two-way analysis of variance, using Bonferroni-Dunn post-hoc ANOVA (Statview, Abacus Concepts, Inc., Berkeley, Calif.). The criterion for significance in all cases was a p value $\leq 0.05$.

EXAMPLE 2

Regulation of Trabecular Meshwork Cell $Na^+$—$K^+$—$2Cl^-$ Cotransport Activity The hypothesis that hormones and neurotransmitters can modulate trabecular meshwork cell volume by altering $Na^+$—$K^+$—$2Cl^-$ cotransport activity requires that these agents alter the net uptake of Na, K and/or Cl occurring via the cotransporter.

The effects of hormones, neurotransmitters and second messengers on Bumetanide-sensitive K influx of bovine trabecular meshwork cells were assessed using the procedures of Example 1. The cells were preincubated and assayed in the presence of vasopressin (100 nM) (Peninsula Laboratories, Belmont, Calif.); norepinephrine (NE) (10 $\mu$M) (Sigma Chemical, ST. Louis, Mo.); acetylcholine (Ach) (1 $\mu$M) (Signa), 8-bromo-cyclic AMP (cAMP) (50 $\mu$M) (Sigma); 8-bromo-cyclic GMP (cGMP, 50 $\mu$M) (Sigma); A23 187 (1 $\mu$M) (Sigma); phorbol 12-myristate 13-acetate (PMA) (10 nM) (Sigma); or Ca-free medium plus 5 $\mu$M 1,2-bis (o-aminophenoxy)ethane-N,N,N',N-tetraacetic acid acetoxymethyl ester (BAPTA-AM), following a 30 minute pre-exposure of the cells to the membrane permeant Ca chelator BAPTA-AM. The control is the Hepes-buffered medium containing Na, K, Cl, CA and other ions as described in Example 1B. In Table 3 below the results of these studies are shown as $\mu$mol/g protein/min. The data represent the mean values±SEM of quadruplicate determinations from two experiments.

TABLE 3

BUMETANIDE-SENSITIVE K INFLUX ($\mu$mol/g protein/min)

| Control | 25.6 ± 0.71 | NE | 18.6 ± 1.79 |
| --- | --- | --- | --- |
| VP | 40.4 ± 1.05 | Ach | 20.2 ± 1.26 |
| A23187 | 33.4 ± 5.33 | cAMP | 19.6 ± 0.96 |
| PMA | 34.0 ± 1.33 | cGMP | 19.7 ± 0.74 |
| Ca-free | 4.9 ± 1.06 | | |

The data in Table 3 show that exposure of the cells to the divalent cation ionophore A23187 at a concentration of 1 $\mu$M to elevate intracellular $Ca^{2+}$ caused stimulation of Na—K—Cl cotransport activity. When the cells were preincubated for 30 minutes with BAPTA-AM at a concentration of 5 $\mu$M, and subsequently assayed in the presence of BAPTA-AM and Ca-free medium, activity of the $Na^+$—$K^-$—$2Cl^-$ cotransporter was markedly reduced. Activation of protein kinase C by assaying the cells in the presence of the phorbol ester phorbol 12-myristate 13-acetate also stimulated cotransport in these cells. Exposure of the cells to vasopressin also stimulated cotransport activity. In contrast, exposure of the cells to the permeable cyclic nucleotides 8-Br-cyclic AiMP (50 $\mu$M) or 8-Br-cyclic GMP (50 $\mu$M) caused inhibition of bumetanide-sensitive K influx, as did exposure to either norepinephrine or acetylcholine.

EXAMPLE 3

Effect of Extracellular Hypertonicity on Trabecular Meshwork Cell Volume and $Na^+$—$K^+$—$2Cl^-$ Cotransport Activity The hypothesis that the Na—K—Cl cotransport system of trabecular meshwork cells participates in restoration of cell volume following hypertonicity-induced cell shrinkage by mediating a compensatory re-swelling of the cells requires that the cotransporter be stimulated by cell shrinkage. Also, extracellular tonicity should be directly related to cotransport activity, with the greatest sensitivity occurring within a physiological range (i.e., approximately 270–330 mOsm). That is, the largest changes in cotransport activity should be elicited by relatively small changes in osmolarity in the range of 300 mOsm (rather than at 400 mOsm, for example). A role for Na—K—Cl cotransport in mediating cell shrinkage-induced regulatory volume increase also requires that cell shrinkage cause an increase in cell Na, K and Cl content by stimulating net uptake of these ions by the cotransporter following exposure of the cells to hypertonicity in the presence and absence of bumetanide.

Figure 3A:
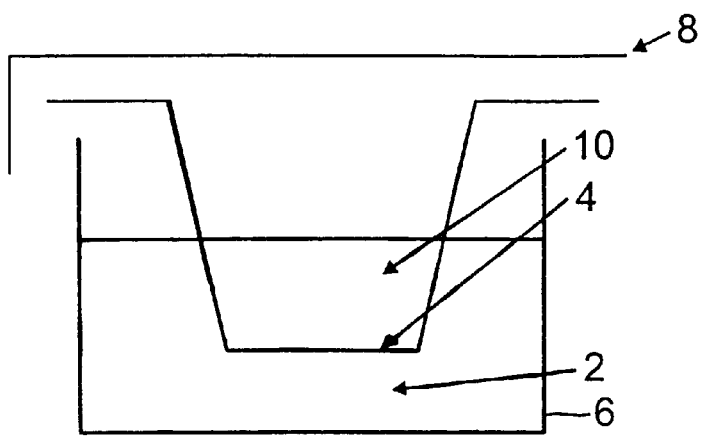
FIG. 3A is a schematic diagram of cell culture chambers with filter inserts.
Figure 3B:
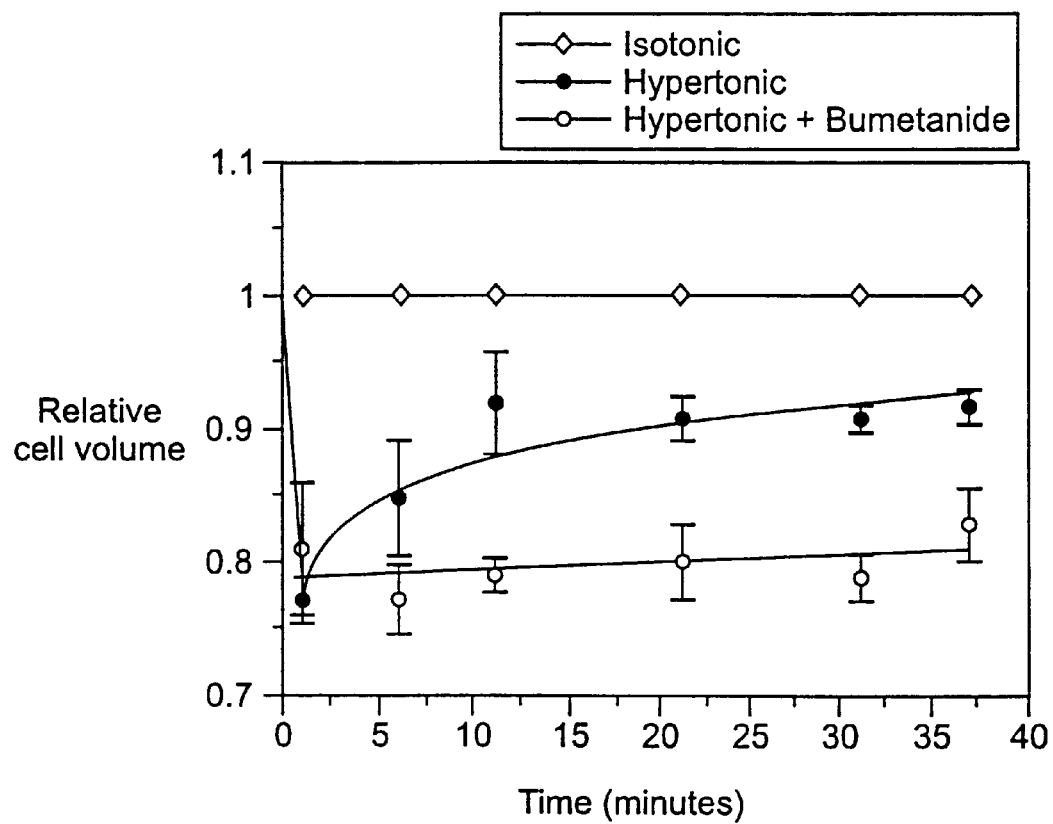
FIG. 3B is a graph comparing the effect of isotonic (300 mOsm ) or hypertonic (400 mOsm) medium upon the relative cell volume of confluent bovine TM cells in isotonic (300 mOsm) (—◊—) or hypertonic (400 mOsm) (—●—) medium with the hypertonic medium containing bumetanide (—○—). Mean cell volume was determined over the time course shown by electronic cell sizing with a Coulter Counter. Data are mean values±SEM, n=4.
Figure 3C:
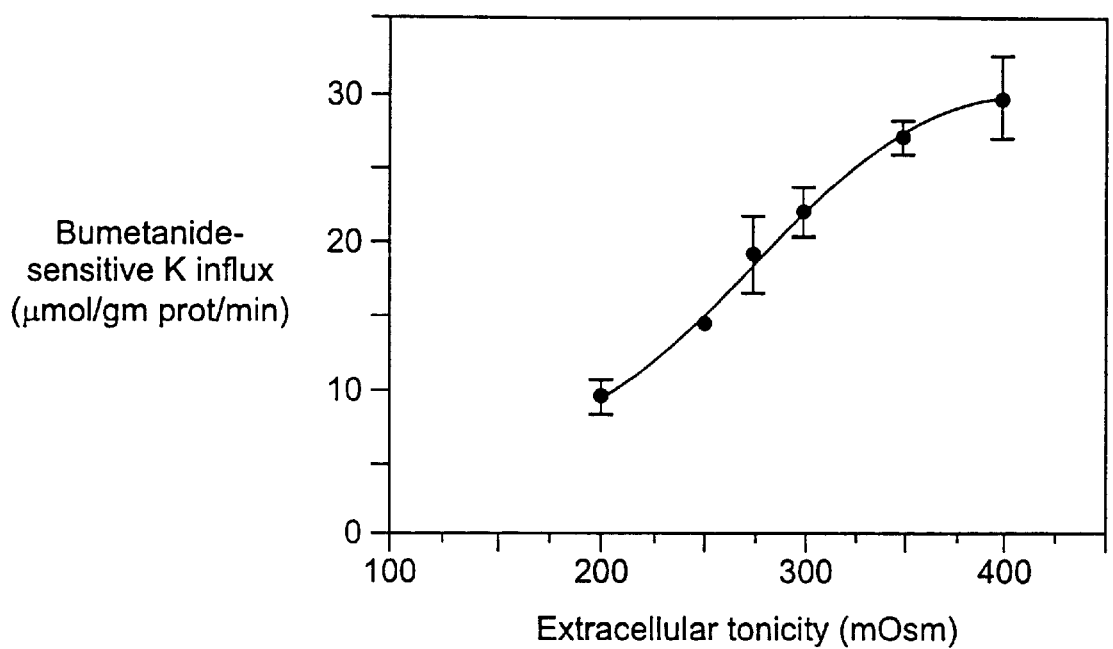
FIG. 3C is a graph showing the effect upon bumetanide-sensitive K influx in bovine TM cell monolayers of changes in extracellular tonicity (mOsm) caused by addition of NaCl. Data are mean values±SEM, n=4.

In order to determine whether the Na—K—Cl cotransporter of TM cells may play a role in restoration of intracellular volume following hypertonicity-induced cell shrinkage, we evaluated the effect of hypertonicity on TM cell volume and $Na^+$—$K^+$—$2Cl^-$ cotransport activity. As shown in FIG. 3, exposure of the cells to hypertonic medium caused an immediate shrinkage of cells (as determined by Coulter Counter) to approximately 70% of control isotonic volume (at 1 minute, the earliest measurement). The intracellular volume of the cells then increased over a slower time course, with volume recovering to approximately 84% by 33 minutes as shown in FIG. 3A.

When the hypertonic medium contained bumetanide, however, the volume recovery was greatly attenuated. This suggests that the cotransporter of TM cells contributes to restoration of intracellular volume following hypertonicity-induced cell shrinkage. Consistent with the theory, as shown in FIG. 3B, we found that exposure of the TM cells to hypertonicity also caused stimulation of $Na^+$—$K^+$—$2Cl^{31}$ cotransport activity. Maximal stimulation by hypertonicity was observed between 350 and 400 mOsm.

EXAMPLE 4

Male albino New Zealand rabbits weighing $\geq 2$ Kg were used for in vivo experiments performed under various active animal use protocols approved by the Institutional Animal Care and Use Committee at UC Davis. Animals were sedated with an intravenous dose of Napentabarbitol, 1–2 mg/Kg to permit their handling and frequent measurement of intra-ocular pressure (IOP). Topical anesthesia consisting of Proparacaine HCl (Alcaine™) was used for IOP measurements. A pneunatonometer (Mentor O & O Classic Model 30 Penumatonometer™, Norwell, Mass.) calibrated to a known (25 mmHg) pressure prior to each experiment was used for all IOP measurements. This model of Pneumatonometer provides a readout of standard deviation of each measurement; only measurements with a standard deviation of $\leq 1$ mmHg were accepted and most were less than 0.5 mmHg. Following sedation, IOP measurements were carried out over at least 30 minutes to assure that a stable baseline IOP was present.

Drugs and/or vehicle was administered to one eye of each animal via subconjunctival injection in order to bypass any barriers to drug penetration, such as an intact corneal and conjunctival epithelium and to achieve rapid and high concentrations of drug, bypassing epithelial barriers. The contralateral eye treated only with vehicle served as a control for each animal. Two syringes were prepared for each experiment, one containing drug and vehicle, the other containing only vehicle. Using topical anesthetic, 0.1 cc from each syringe was injected subconjunctivally into the superior aspect of the globe at the 12:00 o'clock position. Injections raised a prominent bleb, confirming subconjunctival placement of the drug or vehicle. This bleb then smoothed out over about ten minutes, indicating diffusion of the drug or vehicle throughout the subconjunctival space.

Measurements of intra-ocular pressure were taken at various intervals following the subconjunctival administration of the drug and/or vehicle. IOP in both eyes fluctuated over time reflecting the level of anesthesia. During the course of the experiment, the animal handlers and investigators were masked as to which eye had received the drug or control injection.

Figure 5A:
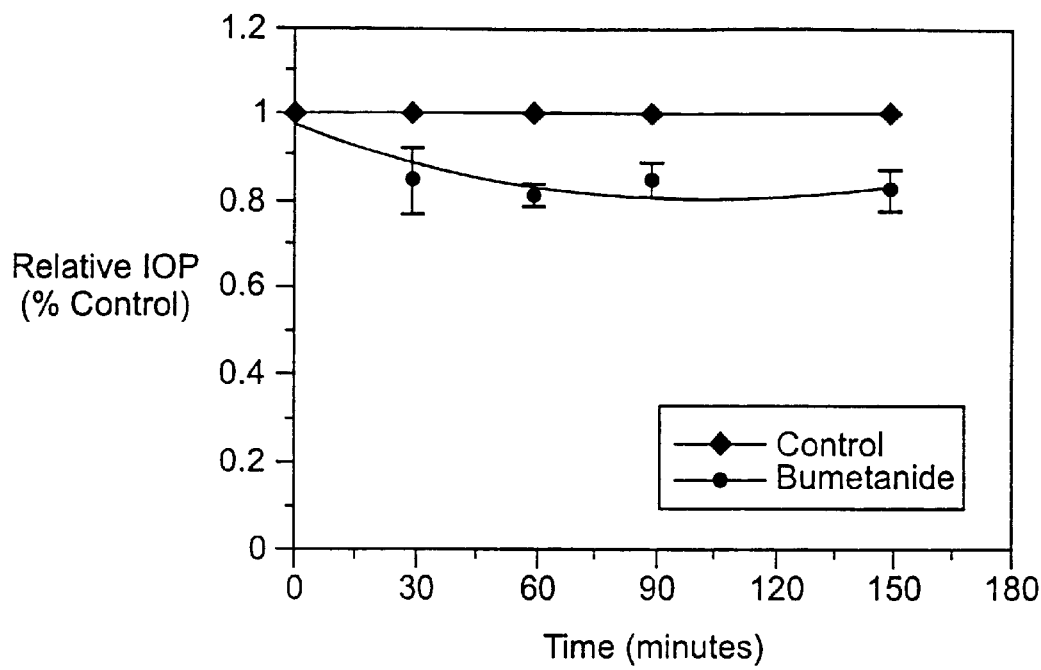
FIG. 5A is a graph showing the effect over time upon intra-ocular pressure (IOP) of bunetanide (—♦—) versus vehicle (control) (------) instilled into the eve of a rabbit (n=1).
Figure 5B:
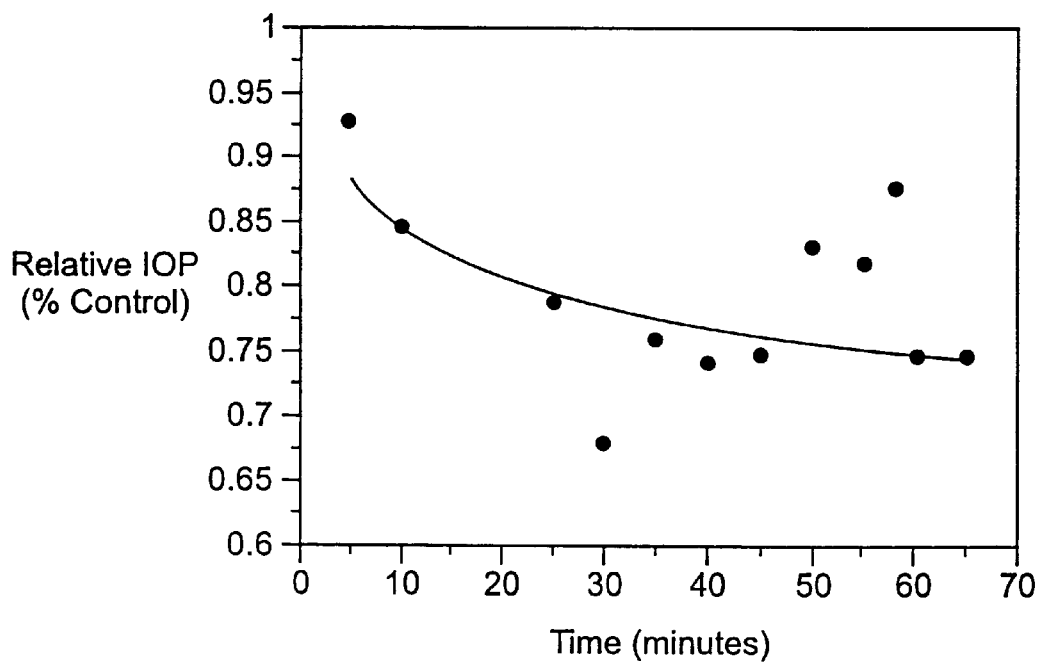
FIG. 5B is a graph showing the effect over time upon IOP of bumetanide instilled into the eye of a second rabbit.

Two animals were treated with bumetanide prepared from the powder form to produce a concentration of $10^{-5}$ M, in a vehicle of DMSO. The control was treated with DMSO alone. Subconjunctival injections with a total volume of 0.1 cc were given to each eye. As shown by the data summarized in FIG. 5A, in the first animal treated with drug the effect of bumetanide on IOP was rapid and pronounced and lasted beyond two hours. As shown in FIG. 5B, in the second animal treated with drug, the average drop in IOP is even more pronounced. Data are expressed as a %-lowering of IOP relative to the contralateral, control eye. The FDA requires a 20% lowering of IOP for a drug to be considered clinically effective in the treatment of glaucoma and ocular hypertension.

Figure 6:
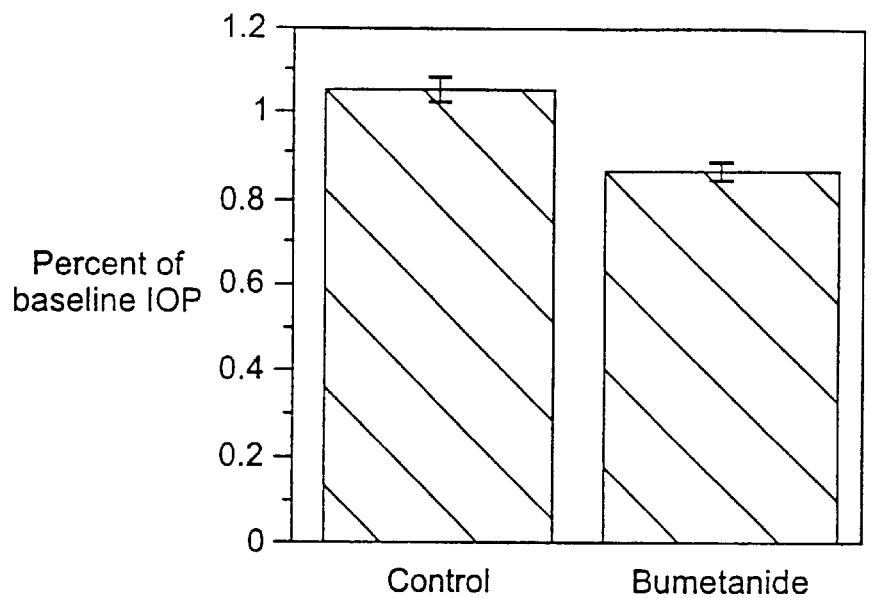
FIG. 6 is a bar graph comparing the average IOP-lowering effect of control and bumetanide calculated as the percent of baseline IOP.

FIG. 6 compare the average of two experiments (2 animals tested with bumetanide, 2 tested with torasemide) and reveals an average IOP lowering effect of over 20%.

EXAMPLE 5

Figure 7:
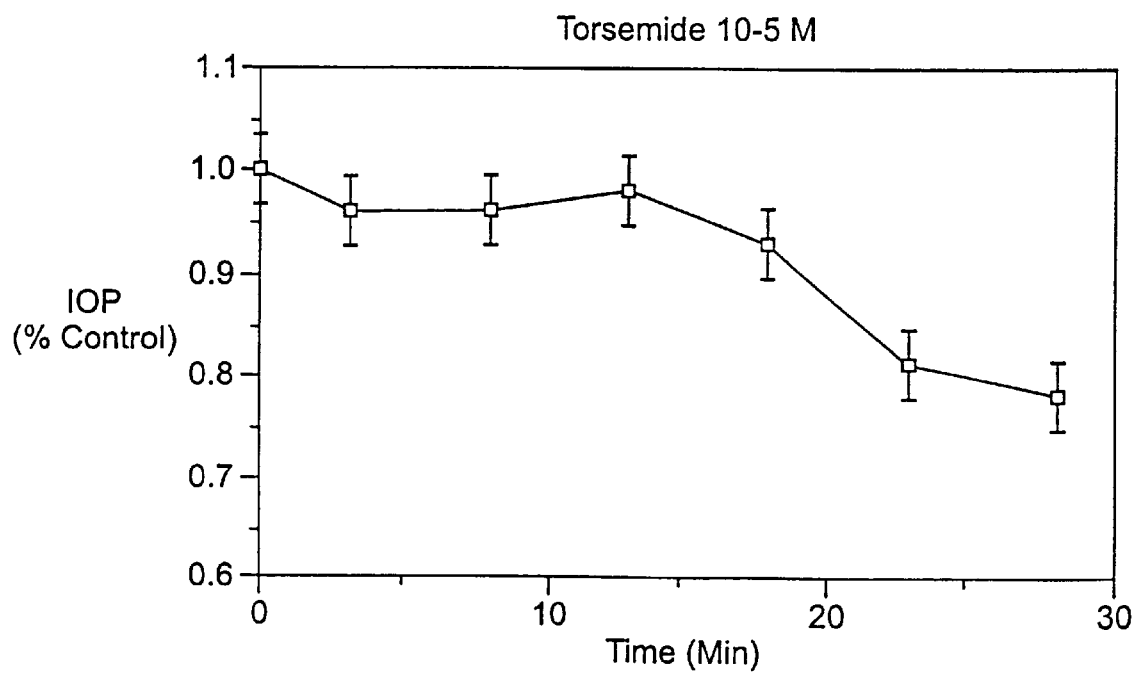
FIG. 7 is a graph showing the percent reduction of intra-ocular pressure over time upon in vivo administration of torasemide.

Using the protocol described in Example 4 above, 0.1 cc of 1 μM torasemide (Burroughs Wellcome Co., Greenville, N.C. for Boehringer-Mannheim Pharmaceuticals, Rockville, Md.) diluted from the commercially-available 29 mM stock intravenous form with phosphate-buffered saline. The commercial vehicle contained polyethylene glycol (PEG) and Tris in unknown amounts. Following the rather large dilution, the concentrations of Tris and PEG would have been negligible. Therefore the phosphate buffered saline was used as the control vehicle. As can be seen by the results summarized in FIG. 7, torasemide produced an IOP-lowering effect with a time course and magnitude similar to that seen with bumetanide.

EXAMPLE 6

Figure 8:
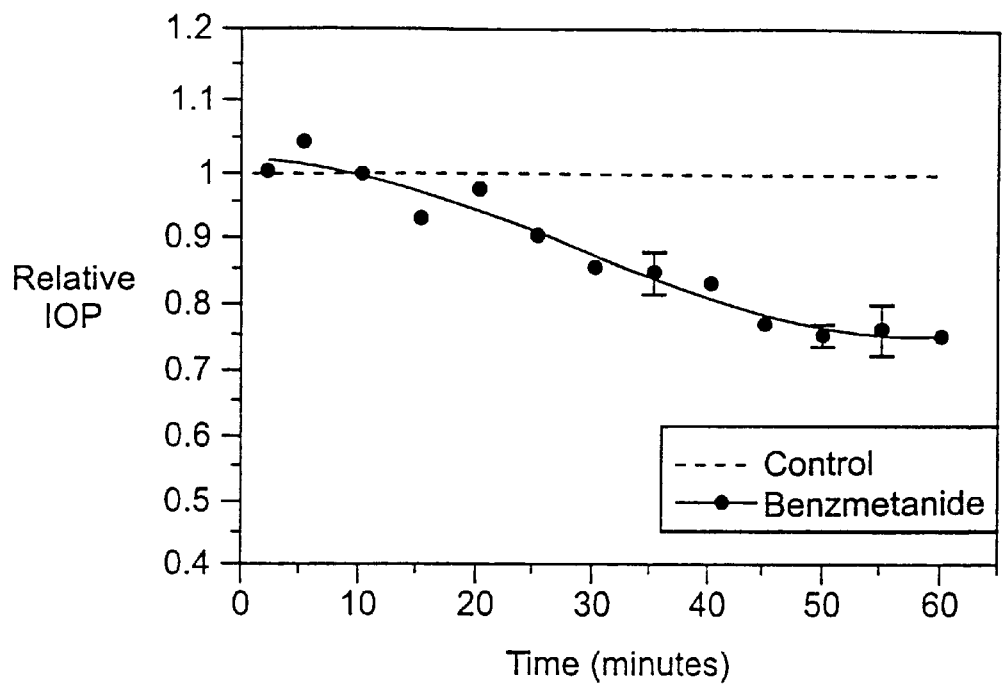
FIG. 8 is a graph showing the percent reduction of intra-ocular pressure over time upon in vivo administration of benzmetanide (—●—) as compared with control (------).

Using the protocol described in Example 4 above with male albino New Zealand rabbits, one animal was treated by subconjunctival injection in one eye with 0.1 cc of 7.5 μM benzmetanide, prepared by diluting from a 5 mM stock solubilized in DMSO into phosphate-buffered saline with the final amount of DMSO present at 0.15%. The contralateral control eye was treated by subconjunctival injection of 0.1 cc of phosphate-buffered saline with the final amount of DMSO present at 0.15%. The control was treated with phosphate-buffered saline with 0.15% DMSO alone. As shown in FIG. 8, benzmetanide caused a significant drop in intra-ocular pressure. Pressure in the presence of benzmetanide is plotted relative to pressure observed in the contralateral, control eye (as a percentage of the IOP measured in the control eye at the same time point). A significant reduction of IOP was observed after 15 minutes. A 24% decrease in IOP was observed after 50 minutes with IOP remaining at that level through the end of the experiment at 60 minutes.

Figure 9:
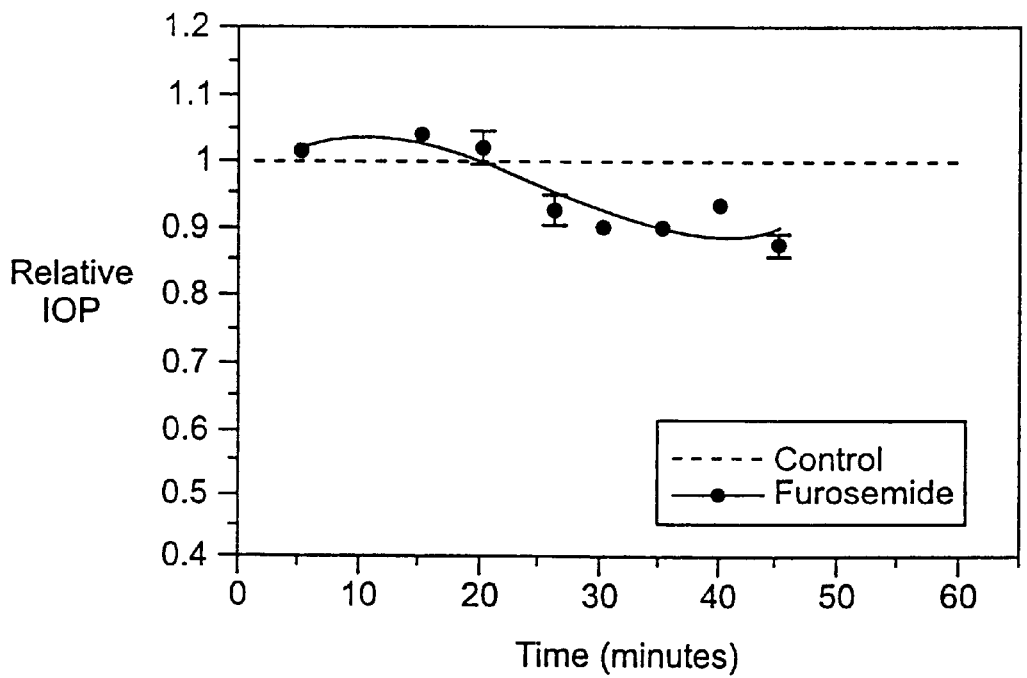
FIG. 9 is a graph showing the percent reduction of intra-ocular pressure over time upon in vivo administration of furosemide (—●—) as compared with control (------).

In a separate experiment using the same protocol, furosemide was the test drug. One animal was treated in the test eye by subconjunctival injection of 0.1 cc of 100 μM furosemide, prepared by diluting from a 0.1 M stock solubilized in DMSO into phosphate-buffered saline, with the final amount of DMSO present at 0.1%. The contralateral control eye received 0.1 cc of phosphate-buffered saline containing 0.1% DMSO alone by subconjunctival injection. As shown in FIG. 9, furosemide caused a significant drop in relative IOP 25 minutes after injection. The maximal inhibition of 12.4% was observed in the furosemide-treated eye. The experiment was ended at 45 minutes.

Figure 10:
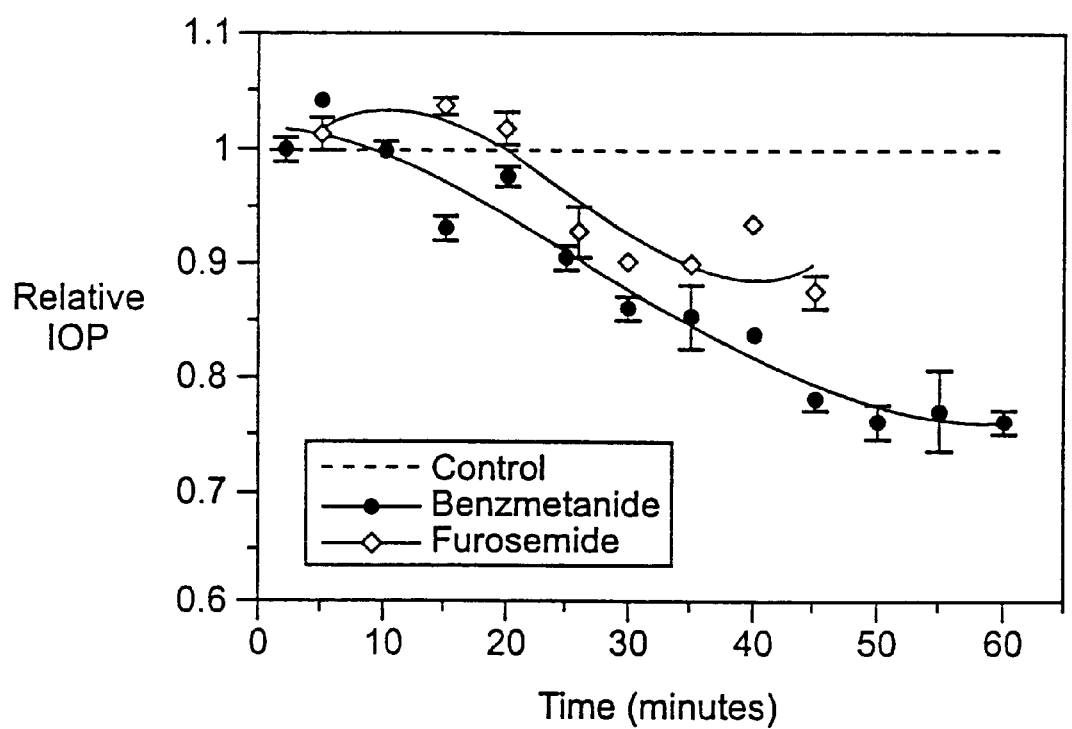
FIG. 10 is a graph comparing the percent reduction of intra-ocular pressure over time upon in vivo administration of benzmetanide (—●—) or furosemide (—◊—) as compared with control (------).

As shown by comparison of the two tests in FIG. 10, furosemide had a slower onset and a less pronounced effect on IOP than did benzmetanide. This is consistent with the relative differences in potency for furosemide and benzmetanide as inhibitors of $Na^+$—$K^+$—$2Cl^-$ cotransport activity (e.g. see S. M. O'Grady et al., supra).

The foregoing description of the invention is exemplary for purposes of illustration and explanation. It should be understood that various modifications can be made without departing from the spirit and scope of the invention. Accordingly, the following claims are intended to be interpreted to embrace all such modifications.

What is claimed is:

1. A method for increasing aqueous humor outflow in the eye of a mammalian patient to reduce the intra-ocular pressure therein, said method comprising administering to said eye a composition comprising an effective amount of a compound that inhibits the $Na^+$—$K^+$—$2Cl^-$ co-transporter in the trabecular meshwork of the eye, or a pharmaceutically acceptable salt thereof.

2. The method of claim 1 wherein the patient is human and administration is in treatment of glaucoma.

3. The method of claim 2 wherein dosage of the compound is 50–100 microliters of a 5–10 mM solution of the compound per day.

4. A method for increasing aqueous humor outflow in the eye of a mammalian patient to reduce the intra-ocular pressure therein, said method comprising administering to said eye a composition comprising an effective amount of a compound that inhibits the $Na^+$—$K^+$—$2Cl^-$ co-transporter in the trabecular meshwork of the eye, said compound selected from the group consisting of high ceiling diuretics.

5. The method of claim 4 wherein the compound is selected from the group consisting of furosemide, torasemide, piretanide and pharmaceutically acceptable salts thereof.

6. The method of claim 4 wherein the compound is furosemide, or a pharmaceutically acceptable salt thereof.

7. The method of claim 4 wherein the compound is torasemide, or a pharmaceutically acceptable salt thereof.

8. The method of claim 4 wherein the composition is administered by microinjection.

9. The method of claim 4 wherein the composition further comprises a pharmaceutically acceptable carrier.

10. The method of claim 4 wherein the composition is administered topically.

11. The method of claim 10 wherein the composition further comprises a compound that enhances corneal penetration.

12. The method of claim 11 wherein the compound has an octanol:water coefficient of at least 0.005.

13. The method of claim 12 wherein dosage of the compound is 50–100 microliters of a 5–10 mM solution of the compound per day.

14. The method of claim 10 wherein the composition further comprises 0.025% benzalkonium chloride.

15. The method of claim 10 wherein the compound is selected from the group of lipophilic derivatives of furosemide, piretanide, and torasemide.

16. The method of claim 15 wherein the compound has an octanol:water coefficient of at least 0.01.

17. The method of claim 16 wherein the compound is a lipophilic derivative of torasemide.

18. The method of claim 16 wherein the compound is a lipophilic derivative of furosemide.

19. The method of claim 16 wherein the compound is a lipophilic derivative of piretanide.

20. The method of claim 4 wherein the patient is human and administration is in treatment of glaucoma.

21. The method of claim 20 wherein dosage of the compound is 50–100 microliters of a 5–10 mM solution of the compound per day.

22. The method of claim 2 wherein the compound is piretanide, or a pharmaceutically acceptable salt thereof.

* * * * *